(12) United States Patent
Uhr et al.

(10) Patent No.: US 9,901,582 B2
(45) Date of Patent: *Feb. 27, 2018

(54) POLYMORPHISMS IN ABCB1 ASSOCIATED WITH A LACK OF CLINICAL RESPONSE TO MEDICAMENTS

(71) Applicant: Max-Planck-Gesellschaft zur Förderung der Wisenschaften e. V., München (DE)

(72) Inventors: Manfred Uhr, Stockdorf (DE); Florian Holsboer, München (DE); Bertram Müller-Myhsok, München (DE)

(73) Assignee: Max-Planck-Gesellschaft zur Foerderung der Wissenschaften e. V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/800,848

(22) Filed: Jul. 16, 2015

(65) Prior Publication Data
US 2016/0067262 A1 Mar. 10, 2016

Related U.S. Application Data

(62) Division of application No. 12/663,997, filed as application No. PCT/EP2008/004737 on Jun. 12, 2008, now Pat. No. 9,115,398.

(60) Provisional application No. 60/943,335, filed on Jun. 12, 2007.

(51) Int. Cl.
*C12Q 1/68* (2006.01)
*A61K 31/55* (2006.01)
*A61K 31/137* (2006.01)
*A61K 31/343* (2006.01)

(52) U.S. Cl.
CPC ............ *A61K 31/55* (2013.01); *A61K 31/137* (2013.01); *A61K 31/343* (2013.01); *C12Q 1/6883* (2013.01); *C12Q 2600/106* (2013.01); *C12Q 2600/156* (2013.01); *C12Q 2600/172* (2013.01)

(58) Field of Classification Search
None
See application file for complete search history.

(56) References Cited

FOREIGN PATENT DOCUMENTS

WO 2005108605 A 11/2005

OTHER PUBLICATIONS

Andiappan (BMC Genetics. 2010. 11: 36).*
Thomas B. Ejsing et al. "Influence of P-glycoprotein inhibition on the distribution of the tricyclic antidepressant nortriptyline over the blood-brain barrier" Human Psychopharmacology, vol. 20, No. 2, Mar. 2005, pp. 149-153

C. Marzolini et al., "Polymorphisms in Human MDR1 (P-Glycoprotein): Recept Advances and Clinical Relevance" Clinical Pharmacology & Therapeutics, Mosby-Year Book, vol. 75, No. 1, Jan. 1, 2004, pp. 13-33.
Manfred Uhr et al., "Polymorphisms in the drug transporter gene ABCB1 predict antidepressant treatment response in depression" Neuron, vol. 57, No. 2, Jan. 2008, pp. 203-209.
Nicole Soranzo et al., "Identifying candidate causal variants responsible for altered activity of the ABCB1 multidrug resistence gene" Genome Research, vol. 14, No. 7, Jul. 2004, pp. 1333-1344.
Database JSNP ID: ssj0000032.
John et al., Am J. Human Genet., Jul. 2004, vol. 75, No. 1, pp. 54-64.
Chang et al., "Rapid Identification of P-glycoprotein Substrates and Inhibitors", Drug Metabolism and Disposition, vol. 34, No. 12, 2006, pp. 1976-1984.
Dong et al., "Sequence variations of ABCB1, SLC6A2, SLC6A3, SLC6A4, CREB1, CRHR1 and NTRK2: association with major depression and antidepressant response in Mexican-Americans", Molecular Psychiatry (2009), 14, pp. 1105-1118.
Huang et al., "ABCB6, ABCB1 and ABCG1 genetic polymorphisms and antidepressant response of SSRIs in Chinese depressive patients", Pharmacogenomics (2013), 14 (14), pp. 1723-1730.
Kato et al., "ABCB1(MDR1) gene polymorphisms are associated with the clinical response to paroxetine in patients with major depressive disorder", Neuro-Psychopharmacology & Biological Psychiatry 32 (2008), pp. 398-404.
Lin et al., "ABCB1 gene polymorphisms are associated with the severity of major depressive disorder and its response to escitalopram treatment", Pharmacogenetics and Genomics, 2011, 21, pp. 163-170.
Nikisch et al., "Citalopram enantiomers in plasma and cerebrospinal fluid of ABCB1 genotyped depressive patients and clinical response: A pilot study", Pharmacological Research, 58, (2008), pp. 344-347.
Sarginson et al., "ABCB1 (MDR1) polymorphisms and antidepressant response in geriatric depression", Pharmacogenetics and Genomics, 2010, 8 pgs.
Seelig, "A general pattern for substrate recognition by P-glycoprotein", Eur. J. Biochem., vol. 251, (1998), pp. 252-261.
Singh et al., "ABCB1 polymorphism predicts escitalopram dose needed for remission in major depression", Translational Psychiatry (2012), 6 pgs.
Uhr et al., "Polymorphisms in the Drug Transporter Gene ABCB1 Predict Antidepressant Treatment Response in Depression", Neuron 57, Jan. 24, 2008, pp. 203-209.
Cascorbi et al., "Frequency of single nucleotide polymorphisms in the P-glycoprotein drug transporter MDR1 gene in white subjects", Clin. Pharmacol. Ther. 69, pp. 169-174, 2001.
Eichelbaum et al., "Clinical aspects of the MDR1 (ABCB1) gene polymorphism", Ther. Drug. Monit. 26, pp. 180-185, 2004.
Grauer and Uhr, "P-glycoprotein reduces the ability of amitriptyline metabolites to cross the blood brain barrier in mice after a 10-day administration of amitriptyline", J. Psychopharmacol. 18, pp. 66-74, 2004.

(Continued)

*Primary Examiner* — Jehanne S Sitton
(74) *Attorney, Agent, or Firm* — Rothwell, Figg, Ernst & Manbeck, P.C.

(57) ABSTRACT

The present invention relates to methods, compositions, kits and reagents for determining the prognosis of a clinical response in a human patient to a medicament which acts in the central nervous system (CNS) and which is a substrate of the ABCB1 protein. Further, the invention relates to a combination of medicaments for the treatment of human patients having specific polymorphisms in the ABCB1 gene.

8 Claims, 21 Drawing Sheets

(56) References Cited

OTHER PUBLICATIONS

Figure 1:
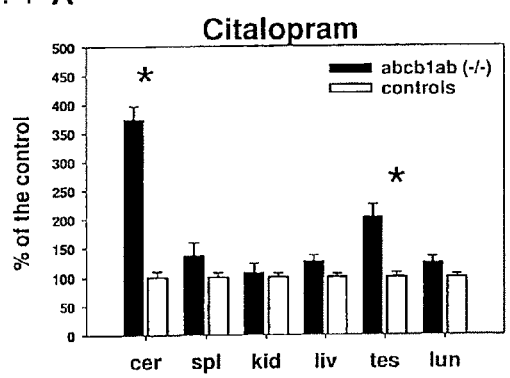
Figure 1:
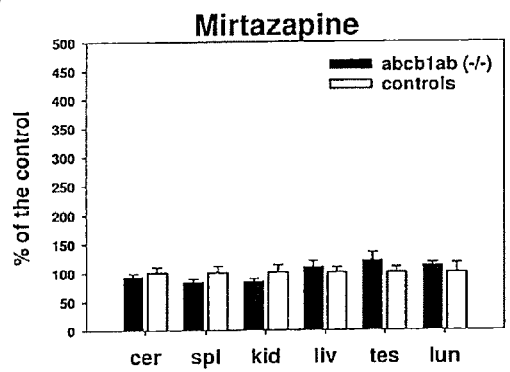
Figure 1:
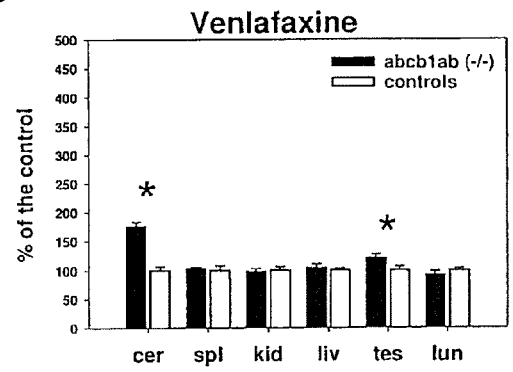
Figure 1:
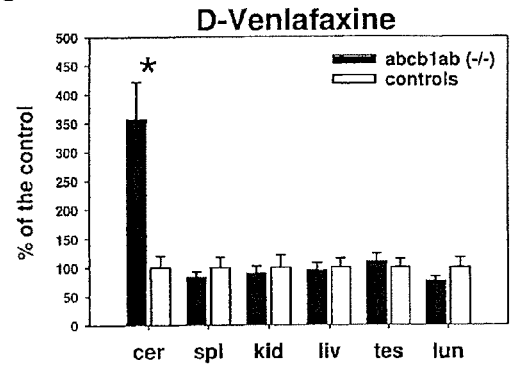

Hoffmeyer et al., "Functional polymorphisms of the human multidrug resistance gene: multiple sequence variations and correlation of one allele with P-glycoprotein expression and activity in vivo", Proc. Natl. Acad. Sci. USA 97, pp. 3473-3478, 2000.

Ito et al., "Polymorphism of the ABC transporter genes. MDR1, MRP1 and MRP2/cMOAT, in healthy Japanese subjects", Pharmacogenetics 11, pp. 175-184, 2001.

Kim et al., "Identification of functionally variant MDR1 alleles among European Americans and African Americans", Clin. Pharmacol. Ther. 70, pp. 189-199, 2001.

Kioka et al. "P-glycoprotein gene (MDR1) cDNA from human adrenal: normal P-glycoprotein carries Gly185 with an altered pattern of multidrug resistance", Biochem. Biophys. Res. Commun. 162, pp. 224-231, 1998.

Mickley et al., "Genetic polymorphism in MDR-1: a tool for examining allelic expression in normal cells, unselected and drug selected cell lines, and human tumors". Blood 91, pp. 1749-1756, 1989.

Stein et al., "Point mutations in the mdr1 promoter of human osteosarcomas are associated with in vitro responsiveness to multidrug resistance relevant drugs", Eur. J. Cancer 30A pp. 1541-1545, 1994.

Tanabe et al., "Expression of P-glycoprotein in human placenta: relation to genetic polymorphism of the multidrug resistance (MDR)-1 gene", J. Pharmacol. Exp. Ther. 297, pp. 1137-1143, 2001.

Uhr et al., "Penetration of amitriptyline, but not of fluoxetine. into brain is enhanced in mice with blood-brain barrier deficiency due to mdr1a P-glycoprotein gene disruption", Neuropsychopharmacology 22, pp. 380-387, 2000.

Uhr et al., "Penetration of endogenous steroid hormones corticosterone, cortisol, aldosterone and progesterone into the brain is enhanced in mice deficient for both mdr1a and mdr1b P-glycoproteins", J. Neuroendocrinol. 14, pp. 753-759, 2002.

Uhr and Grauer, "abcb1ab P-glycoprotein is involved in the uptake of citalopram and trimipramine into the brain of mice", J. Psychiatr. Res. 37, pp. 179-185, 2003.

Uhr et al., "Differential enhancement of antidepressant penetration into the brain in mice with abcb1ab (mdr1ab) P-glycoprotein gene disruption", Biol. Psychiatry 54, pp. 840-846, 2003.

Uhr et al., "P-glycoprotein is a factor in the uptake of dextromethorphan, but not of melperone, into the mouse brain: evidence for an overlap in substrate specificity between P-gp and CYP2D6", J. Psychopharmacol. 18, pp. 509-515, 2004.

Uhr et al., "The anti-Parkinson drug budipine is exported actively out of the brain by P-glycoprotein in mice", Neurosci. Lett. 383, pp. 73-76, 2005.

Uhr et al., "Blood-brain barrier penetration and pharmacokinetics of amitriptyline and its metabolites in P-glycoprotein (abcb1ab) knock-out mice and controls", J. Psychiatric Res. 41, pp. 179-188, 2007.

Ss23402471 (assay for rs4148740, dbSNP, NCBI, NLM, 2004).

Lakham et al (Epilepsy and Behaviour, vol. 14, 2007, 78-82).

Peters (Peters et al., Biology Reports, 2009, 1:23, pp. 1-4).

\* cited by examiner

Fig. 2 A substrates of P-gp   Fig. 2 B Non-substrates of P-gp
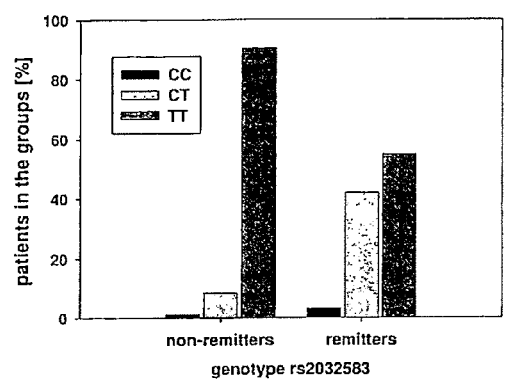
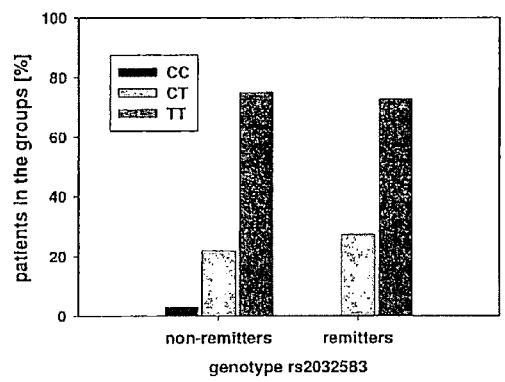

POLYMORPHISMS IN ABCB1 ASSOCIATED WITH A LACK OF CLINICAL RESPONSE TO MEDICAMENTS

This application is a divisional of U.S. Ser. No. 12/663,997 filed Dec. 10, 2009, which is a 35 U.S.C. 371 National Phase Entry Application from PCT/EP2008/004737, filed Jun. 12, 2008, which claims the benefit of U.S. Ser. No. 60/943,335 filed on Jun. 12, 2007, the disclosures of which are incorporated herein in their entirety by reference.

DESCRIPTION

The present invention relates to methods, compositions, kits and reagents for determining the prognosis of a clinical response in a human patient to a medicament which acts in the central nervous system (CNS) and which is a substrate of the ABCB1 protein. Further, the invention relates to a combination of medicaments for the treatment of human patients having specific polymorphisms in the ABCB1 gene.

Major depression constitutes one of the greatest disease burdens world-wide and is anticipated to be the second leading global disease burden by the year 2020 trailing only cardiovascular disease (Murray and Lopez, 1996). Antidepressants are the first line treatment of major depression, but their overall clinical efficacy is unsatisfactory as remission, i.e. full resolution of depressive symptoms, occurs in only about half of the patients after a trial with an adequately dosed single drug. Remission rates even decline following successive treatment failures (Trivedi et al., 2006)).

One of the possible reasons for poor antidepressant response is their inadequate penetration into the central nervous system, which depends on the drug's ability to pass the blood-brain barrier (BBB). This barrier includes active transporters that are expressed at the luminal membrane of the endothelial cells lining the small blood capillaries that form the blood-brain barrier. These molecules actively transport their substrates against a concentration gradient out of the cells back into the blood circulation, thus potentially keeping brain drug concentrations low. One of the best-studied transporter molecules is P-glycoprotein (P-gp) (Cordon-Cardo et al., 1989; Thiebaut et al., 1987). P-gp is a member of the highly conserved super-family of ATP-binding cassette (ABC) transporter proteins (Ambudkar et al., 1999). In humans, this 170-kDa glycoprotein is encoded on chromosome 7 by the ABCB1 gene, also known as the multidrug resistance 1 (MDR1) gene (Callen et al., 1987; Chin et al., 1989). P-gp acts as an active efflux pump for a wide range of compounds including a number of drugs and steroid hormones (Schinkel et al., 1996; Uhr et al., 2000, 2002, 2004, 2005). P-gp at the BBB thus regulates intracerebral concentrations and, by extension, may affect the clinical response of CNS-targeting drugs that are substrates of this transporter.

It was speculated that inter-individual differences in the activity of the ABCB1 gene can account in part for the great variation in clinical response to antidepressants in psychiatric patients, even at comparable plasma levels (Uhr and Grauner, 2003). A further study showed different enhancement of penetration of the antidepressants doxepin, venlafaxine and paroxetine in the brain of mice with an ABCB1ab knockout mutation (Uhr, Grauer and Holsboer, 2003).

Numerous papers describe polymorphisms in ABCB1 (Kioka et al., 1989; Stein et al., 1994; Mickley et al., 1998; Hoffmeyer et al., 2000; Kim et al., 2001; Ito et al., 2001; Cascorbi et al., 2001; Tanabe et al., 2001; Eichelbaum et al., 2004), and a multitude of single nucleotide polymorphisms (SNPs) are listed in public SNP databases.

WO 01/09183 discloses polymorphisms in the human ABCB1 gene for the use in diagnostic tests to improve therapy of established drugs and help to correlate genotypes with drug activity and side effect.

WO 2005/108605 relates to polymorphisms in the ABCB1 gene which are associated with an insufficient clinical response to a CNS active medicament which is a substrate of the ABCB1 protein. Seven single nucleotide polymorphisms (SNPs) in the ABCB1 gene are described, which are associated with clinical response to antidepressant drugs. However, there is no evidence in this document that beside the specific polymorphisms disclosed any further polymorphisms in the ABCB1 gene might be associated with a clinical response to CNS-active medicaments.

Thus, there is still a need for identifying polymorphisms of the ABCB1 gene involved in regulating intracerebral concentrations of CNS-active medicaments. It was the object of the present invention to determine new single nucleotide polymorphisms in the ABCB1 gene which are predictive for treatment course and outcome of CNS-active medicaments, which are ABCB1 transporter substrates.

In the studies on which the present application is based the inventors surprisingly were able to identify several new polymorphisms in the ABCB1 gene, which have a clear and statistically relevant association with an insufficient clinical response to CNS-active medicaments. The inventors succeeded in identifying the SNPs rs4148740, rs10280101, rs7787082, rs4148739, rs11983225, rs10248420 and rs12720067 as particularly responsible for this association. The presence of these particular SNPs proved highly predictive for treatment course and outcome of CNS-active medicaments.

A first aspect of the invention relates to a method for determining the prognosis of a clinical response in a human patient to a central nervous system (CNS)-active medicament which is a substrate of the ABCB1 protein wherein the presence of at least one first polymorphism in the ABCB1 gene of said patient is determined, wherein said first polymorphism is selected from the group consisting of rs4148740, rs10280101, rs7787082, rs4148739, rs11983225, rs10248420 and rs12720067 and combinations thereof.

A further aspect of the invention relates to a diagnostic composition or kit for the prognosis of a clinical response in a human patient to a CNS-active medicament which is a substrate of the ABCB1 protein, comprising at least one primer or probe for determining at least one first polymorphism in the ABCB1 gene in said patient, wherein said first polymorphism is selected from the group consisting of rs4148740, rs10280101, rs7787082, rs4148739, rs11983225, rs10248420, rs12720067 and combinations thereof.

A still further aspect of the invention relates to a microarray for the prognosis of a clinical response in a human patient to a CNS-active medicament which is a substrate of the ABCB1 protein comprising a carrier having immobilized thereto at least one probe for determining at least one first polymorphism in the ABCB1 gene in said patient, wherein said first polymorphism is selected from the group consisting of rs4148740, rs10280101, rs7787082, rs4148739, rs11983225, rs10248420, rs12720067 and combinations thereof.

Still a further aspect of the invention relates to a primer or probe for the prognosis of a clinical response in a human patient to a CNS-active medicament which is a substrate of the ABCB1 protein comprising a carrier having immobilized thereto at least one probe for determining at least one first polymorphism in the ABCB1 gene in said patient, wherein said polymorphism is selected from the group consisting of rs4148740, rs10280101, rs7787082, rs4148739, rs11983225, rs10248420, rs12720067 and combinations thereof.

Finally, a further aspect of the invention relates to a therapeutic composition or kit comprising:
(a) a CNS-active medicament which is a substrate of the ABCB1 protein;
(b) a further medicament which is an inhibitor of the ABCB1 protein for treating a human patient having at least one polymorphism in the ABCB1 gene, wherein said polymorphism is selected from the group consisting of rs4148740, rs10280101, rs7787082, rs4148739, rs11983225, rs10248420, rs12720067 and combinations thereof.

The polymorphisms in the human ABCB1 gene disclosed in the present application have a statistically significant association with a delayed, partial sub-optimal or lacking clinical response to medicaments which act in the central nervous system and which are substrates of the ABCB1 protein. A statistically significant association is preferably $p<0.05$, more preferably $p<0.01$ and most preferably $p<0.001$. The determination of significance may be carried out by a polymorphism/haplotype analysis of a sufficient number, e.g. of at least 40, preferably of at least 80, more preferably of at least 100 normal cases. More preferably the determination of significance may be carried out as described in the Example section.

The polymorphisms of the invention are single nucleotide polymorphisms (SNPs). Preferred SNPs are selected from the group consisting of rs4148740, rs10280101, rs7787082, rs4148739, rs11983225, rs10248420 and rs12720067. Surprisingly it was found that the polymorphisms highly associated with the response to CNS-active medicaments are located in a single haplotype block (FIG. 4). The SNPs rs2235067, rs4188740, rs2032583, rs4148739, rs11983225, rs2235040, rs12720067 as well as the SNPs rs7787082 and rs10248420 exhibited an r-square of >0.8 with each other. All highly associated SNPs are located in introns and with a D' of more than 90% in linkage disequilibrium (LD) with the best examined exon SNPs rs1045642 (C3435T), rs2032582 (G2677T) and rs1128503 (C1236T).

The sequence of the human ABCB1 gene including the introns is described in the human reference sequence of the National Center for Biotechnolgy Information (NCBI). The sequence is accessible in gene databases such of NCBI, or Genomics Browser (UCSC) using the reg. sep #=ONM.000927 or the gene ID ABCB1. With regard to the nomenclature of the polymorphisms it is referred to ABCB1 at chr7:8670884-87180500-(NM_000927) ATP-binding cassette, sub-family B (MDR/TAP), NM #=Reference Sequence Number, Localisation on genome according to the May 2004 human reference sequence (UCSC version hg17) based on NCBI Build 33. All polymorphisms have been selected from the public SNP database of SNP. The location of the SNPs within ABCB, is according to the May 2004 human reference sequence (UCSC version mg 17).

The CNS-active medicaments are preferably selected from the group consisting of antidepressants, anxiolytics, hypnotics, cognitive enhancers, antipsychotics, neuroprotective agents, antiemetics, antiepileptics, antibiotics, anticancer agents, antimycetics, antiparkinson agents, antiviral agents, glucocorticoids, immunosuppressants, statins, neuroleptics, and opioids. A preferred class of medicaments are antidepressants. Examples of CNS-active medicaments are described in Schatzberg and Nemeroff, "The American Psychiatric Publishing Textbook of Psychopharmacology", Amer Psychiatric Pr, 2004.

A preferred class of medicaments are antidepressants. Examples of antidepressants are imipramine, amitriptyline, amitriptylinoxid, bupropion, citalopram, clomipramine, doxepine, desipramine, flesinoxan, fluoxetine, fluvoxamine, maprotiline, mirtazepine, mianserin, moclobemide, nefazodone, nortriptyline, paroxetine, selegiline, sertraline, tranylcypromine, trazodon, trimipramine and, venlafaxine. Preferred examples of antidepressants which are substrate of the ABCB1 protein are amitriptyline, citalopram, doxepine, flesinoxan, nortriptyline, paroxetine, trimipramine, and venlafaxine. Especially preferred examples of antidepressants are citalopram, venlafaxine, amitriptyline or paroxetine.

Further preferred CNS-medicaments are anxiolytics, hypnotics, cognitive enhancers and, antipsychotics. Examples of anxiolytics include but are not limited to alprazolam, bromazepam, clonazepam, diazepam, iorazepam, halazepam, chlordiazepoxide, buspirone, azapirone, pagoclone, prazosin, biperiden and, kava kava. Examples of hypnotics are secobarbital, pentobarbital, methaqualone, ethchlorvynol, chloral hydrate, mebrobamate. Examples of cognitive enhancers are acetyl L-carnitine (ALCAR), adrafinil, aniracetam, deprenyl, galantamine, hydergine, idebenone, modafinil, picamilon, piracetam, pyritinol, vasopressin and, vinpocetine. Examples of antipsychotics are aripiprazol, risperidon, olanzapine, quetiapine and, ziprasidone, chlorpromazine, fluphenazine, trifluoperazine, perphenazine, thioridazine, holoperidol, thiothixene, molindone, loxapine, clozapine, olanzapine, quetiapine, risperidone, sertindole, ziprasidone, amisulpid, aripriprazol, benperidol, chlorpromazine, chlorprothixen, flupentixol, fluspirilen, levomepromazin, benperidol, melperon, perazin, perphenazin, pimozid, pipamperon, sulpirid, triflupromazin, zotepin, zuclopenthixol.

Further preferred examples of substrates of the ABCB1 protein are antiemetics such as domperidone or ondansetron, antiepileptics such as carbamazepine, felbamate, lamotrigin, phenobarbita and phenytoin, antiparkinson agents such as budipin or L-Dopa, neuroleptics such as olanzapine, quetiapine, risperidone and sulpiride, or opioids such as fentanyl or morphine.

The patients to be tested are human patients suffering from a disorder which may be treated with a CNS-active medicament, e.g. a psychiatric disorder. Particularly, the patients have a depressive disorder, dysthymia and/or a bipolar disorder.

The present invention relates to the determination of the prognosis of a clinical response in a human patient. The term "a clinical response" in the present application with regard to antidepressants relates to a remission status after four to six weeks of treatment. Methods of assessing a remission status are well known in the art. For example, remission can be evaluated according to the Hamilton Depression Rating Scale (HAM-D; Hamilton, Br. J. Soc. Clin. Psychol. 6 (1967) 278-296). A HAM-D score of 10 or below is regarded as remission of the depressive symptoms. Remission can also be assessed according to a normalisation of the hypothalamic-pituitary-adrenocortical (HPA) axis. The development and course of depression is causally linked to impairments in the central regulation of the HPA axis. Abnormalities in the HPA axis can be measured using the dexamethasone-suppression test (DST) or the combined dexamethasone/corticotropin-releasing hormone (Dex/CRH) test. Changes in cortisol and/or adrenocorticotropic hormone (ACTH) measurements during the DST or Dex/ CRH test are indicative of HPA dysfunction while normalisation of cortisol and or ATCH is indicative of remission (Heuser et al, J. Psychiat. Res. 28 (1994) 341-356; Rybakowski and Twardowska, J. Psychiat. Res. 33 (1999) 363-370; Zobel et al, J. Psychiat. Res. 35 (2001) 83-94; Künzel et al, Neuropsychopharmacology 28 (2003) 2169-2178). Methods and conditions for performing the DST and Dex/ CRH test are well known in the art, see for example Heuser et al, J. Psychiat. Res. 28 (1994) 341-356; Künzel et al, Neuropsychopharmacology 28 (2003) 2169-2178. Briefly, individuals may be pre-treated at 23:00 with an oral administration of 1.5 mg dexamethasone. For the DST test, a blood sample may be drawn at 8:00 prior to dexamethasone administration (i.e. pre-dexamethasone) and at 8:00 the morning following dexamethasone administration (i.e. post-dexamethasone). For the Dex/CRH test, a venous catheter may be inserted at 14:30 the day following dexamethasone administration and blood may be collected at 15:00, 15:30, 15:45, 16:00, and 16:15 into tubes containing EDTA and trasylol (Bayer Inc., Germany). At 15:02, 100 mg of human CRH (Ferring Inc., Germany) may be administered intravenously. Measurement of plasma cortisol concentrations may be done according to known methods, e.g. using a commercial radioimmunoassay kit (ICN Biomedicals, USA). Plasma ACTH concentrations may also be measured according to known methods, e.g. using a commercial immunometric assay (Nichols Institute, USA). With regard to other classes of medicaments, the term "clinical response" may be defined as a reduction of the severity of symptoms by over 50% from the severity of symptoms at the beginning of treatment.

The presence of a polymorphism associated with a delayed, partial, sub-optimal or lacking clinical response to a medicament is preferably determined by a genotyping analysis of the human patient. According to the invention, (a) at least one polymorphism selected from the group consisting of rs4148740, rs10280101, rs7787082, rs4148739, rs11983225, rs10248420 and rs12720067 is determined. In a preferred embodiment of the invention, at least one additional polymorphism (b) being in linkage disequilibrium with at least one of the polymorphisms of (a) is determined. The polymorphisms of (b) being in linkage disequilibrium with the polymorphisms of (a) are preferably selected from the group consisting of rs2235067, rs2032583, rs2235040, and rs2235015.

The genotyping analysis frequently comprises the use of polymorphism-specific primers and/or probes capable of hybridizing with the human ABCB1 gene and allowing a discrimination between polymorphisms, particularly SNPs at a predetermined position. For example, the genotyping analysis may comprise a primer elongation reaction using polymorphism-specific primers as described in the examples. The determination of individual polymorphisms may be carried out by mass-spectrometric analysis as described in the examples. A further preferred embodiment comprises a microarray analysis which is particularly suitable for the parallel determination of several polymorphisms. Suitable microarray devices are commercially available.

According to a further embodiment of the invention the prognosis of a clinical response in a human patient to a CNS-active medicament which is a substrate of the ABCB1 protein can also be determined by detecting a change in the function of the ABCB1 gene. The determination of the transporting activity of the ABCB1 gene product at the blood-brain barrier can be used as an indicator for the clinical response in a human patient to a CNS-active medicament. An assay for detecting a change in the function of the ABCB1 gene may comprise imaging techniques like positron emission tomography (PET) and MR-spectroscopy.

According to a particularly preferred embodiment of the invention, the assay of the transporting activity is accomplished in addition to the determination of the at least one specific polymorphism of the invention described above. Based on the results of polymorphism determination a prognosis of a clinical response in a human patient to a CNS-active medicament which is a substrate of the ABCB1 protein can be made. Thus, on the one hand, if the patient to be tested does not have a polymorphism which is associated with an insufficient clinical response to the medicament, a favourable prognosis for a clinical response can be given and the medicament for obtaining the clinical response may be manufactured, prescribed and administered in a standard dose whereby a sufficient clinical response may be expected with high probability. On the other hand, the patient to be tested may have one or a plurality of polymorphisms which are associated with an unfavourable prognosis for a clinical response of the medicament. If such an unfavourable prognosis for a clinical response is given, a modified therapeutic regimen for the patient may be used. For example, the medicament may be administered in a dose which is higher than the standard dose, e.g. by increasing the dose strength and/or the number of doses to be administered per time interval. Further, the formulation of the medicament may be manufactured and adminstered which shows an increased permeation through the blood-brain barrier, e.g. by including a blood-brain barrier permeation aid such as those indicated in Table 1.

Further, the manufacture and administration of the medicament may be combined with the manufacture and administration of a further medicament which is an inhibitor of the ABCB1 protein. Suitable inhibitors of the ABCB1 protein are known and for example described in US 2003/0073713 A1 which is herein incorporated by reference. Further ABCB1 inhibitors are described in Marzolini C, et al (2004), Clin Pharmacol Ther. 2004 January; 75(1):13-33 which is herein incorporated by reference.

As outlined above, the present invention also relates to diagnostic compositions and kits for the prognosis of a clinical response in a human patient to a CNS-active medicament which is a substrate of the ABCB1 protein. A diagnostic composition or kit preferably comprises (a) at least one primer and/or probe for determining at least one polymorphism selected from the group consisting of rs4148740, rs10280101, rs7787082, rs4148739, rs11983225, rs10248420 and rs12720067. In a preferred embodiment, the diagnostic composition or kit further comprises at least one additional primer and/or probe for determining at least one polymorphism (b) being in linkage disequilibrium with said polymorphism of (a). The additional primer and/or probe is preferably for determining at least one polymorphism selected from the group consisting of rs2235067, rs2032583, rs2235040, and rs2235015. The primers and/or probes may be nucleic acid molecules such as a DNA, an RNA or nucleic acid analogues such as peptide nucleic acids (PNA) or a locked nucleic acids (LNA). The primer and/or probes are selected such that they can discriminate between polymorphisms at the position to be analyzed. Usually, the primers and probes have a length of at least 10, preferably at least 15 up to 50, preferably up to 30 nucleic acid building blocks, e.g. nucleotides. In a preferred embodiment, the composition or kit comprises at least one primer which hybridizes to the human ABCB1 gene under predetermined conditions, e.g. of temperature, buffer, strength and/or concentration of organic solvent, and which allows a specific determination of the polymorphism to be tested.

The composition or kit preferably further comprises an enzyme for primer elongation such as a DNA polymerase, nucleotides, e.g. chain elongation nucleotides such as deoxide nucleoside triphosphates (dNTPs) or chain termination nucleotides such as didesoxynucleoside triphosphates (ddNTPs) and/or labelling groups, e.g. fluorescent or chromogenic labelling groups.

A microarray for the prognosis of a clinical response to a CNS-active medicament comprises a carrier, e.g. a planar carrier or a microchannel device, having immobilized thereto at least one probe which allows a determination of a polymorphism to be tested. Preferably, the microarray carrier has immobilized thereto a plurality of different probes located at different areas on the carrier which are designed such that they can bind nucleic acid molecules, e.g. RNA molecules or DNA molecules, amplification products, primer elongation products, etc. containing the sequence in which the polymorphism to be tested is located. Thus, an identification of the polymorphism to be analyzed by detection of a site-specific binding events of the nucleic acid sample molecule to the probe immobilized on the carrier may be accomplished.

Finally, the present invention relates to a therapeutic composition or kit comprising a CNS-active medicament which is a substrate of the ABCB1 protein in a therapeutically effective dose and a further medicament which is an inhibitor of the ABCB1 protein in a therapeutically effective dose for treating a human patient having at least one polymorphism in the ABCB1 gene associated with a lack of clinical response to said CNS-active medicament. According to the invention, the polymorphism is at least one polymorphism selected from the group consisting of rs4148740, rs10280101, rs7787082, rs4148739, rs11983225, rs10248420 and rs12720067, optionally in combination with at least one additional polymorphism being in linkage disequilibrium with said polymorphism. The additional polymorphism is preferably selected from the group consisting of rs2235067, rs4148740, rs10280101, rs7787082, rs2032583, rs4148739, rs11983225, rs10248420, rs2235040, rs12720067 and rs2235015. The medicaments may be present as a single formulation or as separate formulations, if desired. Pharmaceutically acceptable carriers, diluents or adjuvants may be included. The composition or kit may be administered by any suitable route, e.g. by oral or parenteral administration or any other suitable means.

The schedule of administration and dose of a CNS-active medicament such as, for example an antidepressant drug can vary between patients and are well know in the medical art, see, for example Benkert and Hippius, "Kompendium der Psychiatrischen Pharmakotherapie", Springer Verlag Publishing, 2000; Albers, "Handbook of Psychiatric Drugs: 2001-2002 Edition", Current Clinical Strategies Publishing, 2000. For antidepressants, there are three therapeutic possibilities for individuals that have been genotyped with SNPs in the ABCB1 gene.

1. The dosage of an antidepressant that is a substrate of ABCB1 would be increased. Examples of such antidepressants are, between 10 mg and 100 mg per day, preferably 40 mg, citalopram; between 10 mg and 80 mg per day, preferably 20 mg, paroxetine; between 50 mg and 500 mg per day, preferably 150 mg, venlafaxine; between 25 mg and 300 mg per day, preferably 75 mg, amitriptyline; between 25 mg and 400 mg per day, preferably 75 mg, nortriptyline; between 50 mg and 400 mg per day, preferably 200 mg, fluvoxamine; between 2 mg and 15 mg per day, preferably 10 mg, reboxetine.

2. An alternative antidepressant that is not a substrate of ABCB1 would be administered. Preferred examples include between 15 mg and 100 mg per day, preferably 30 mg, mirtazapine; between 5 mg and 80 mg per day, preferably 20 mg, fluoxetine.

3. An antidepressant that is a substrate of ABCB1 would be combined with an inhibitor or modulator of ABCB1. Examples of inhibitors or modulators of ABCB1 are disclosed in Table 1 and the dosage would be determined according to the manufactured recommendations.

Furthermore, the present invention shall be explained by the following Tables and Figures as well as Examples:

FIGURES

FIGS. 1A-D Blood-organ barrier function for antidepressant drugs

Organ/plasma ratios of drug concentration in abcb1ab (−/−) mice compared to wild-type controls after subcutaneous administration of citalopram FIG. 1(A), mirtazapine FIG. 1(B) or venlafaxine FIGS. 1. (C and D) for 11 days via osmotic pumps. The organ/plasma ratios for citalopram FIG. 1 (A), mirtazapine FIG. 1(B), venlafaxine FIG. 1 (C) and desmethyl-venlafaxine FIG. 1(D) are shown as % of the control. An asterisk indicates a significant difference between the knockout mutants and the control mice (univariate F-tests in MANOVA, p-values <0.05). Cerebrum (cer), spleen (spl), kidney (kid), liver (liv), testes (tes) and lung (lun) were investigated. Values are shown as means±SEM.

FIGS. 2 A-B Distribution of rs2032583 genotypes

Percentage of rs2032583 genotypes in the groups "non-remitters" and "remitters" for patients treated with substrates of P-gp FIG. 2 (A) (amitriptyline, citalopram, paroxetine or venlafaxine) and those treated with non-P-gp substrates FIG. 2 (B) (mirtazapine).

Figure 3:
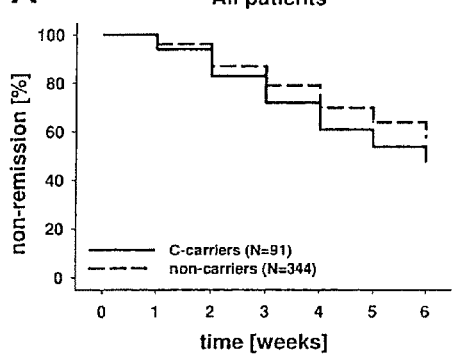
Figure 3D:
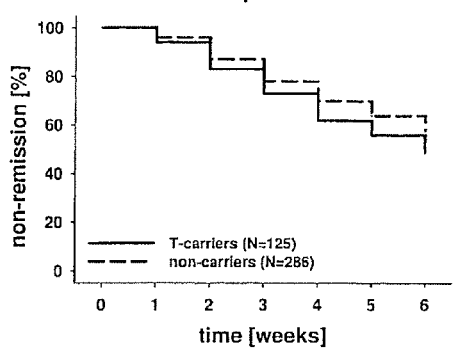
Figure 3:
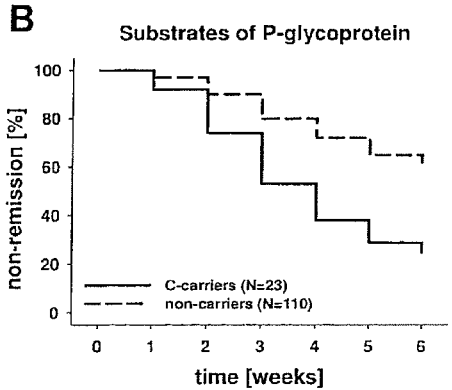
Figure 3E:
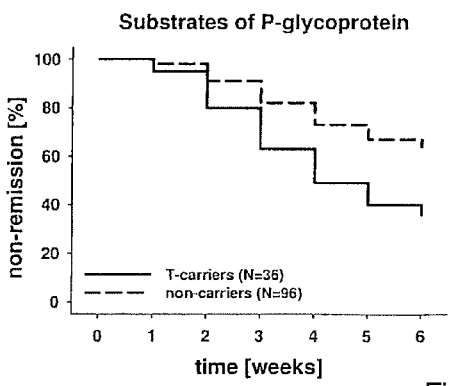
Figure 3:
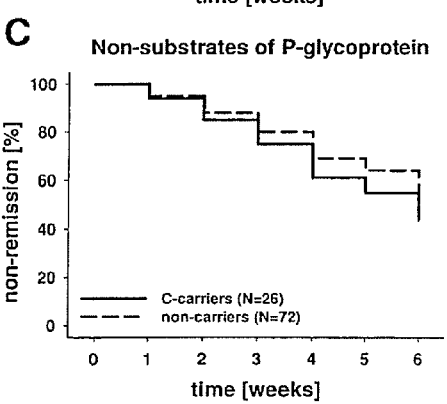
Figure 3F:
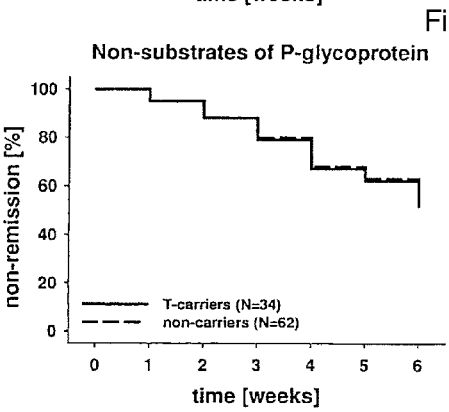

FIGS. 3 A-F Cox regression analysis for rs2032583 and rs2235015

A Cox regression analysis for remission was performed for the SNPs 2032583 FIGS. 3 (A, B, C) and rs2235015 FIGS. 3(D, E, F) dependant from the genetic feature "C-carrier" (rs2032583) or "T-carrier" (rs2235015). The Figure shows the time course of non-remitters, i.e. depressed patients. It depicts the examination of all patients FIGS. 3 (A, D) and the two subgroups of patients receiving substrates of P-gp FIGS. 3 (B, E) and those receiving non-P-gp substrates FIGS. 3 (C, F).

Figure 4A:
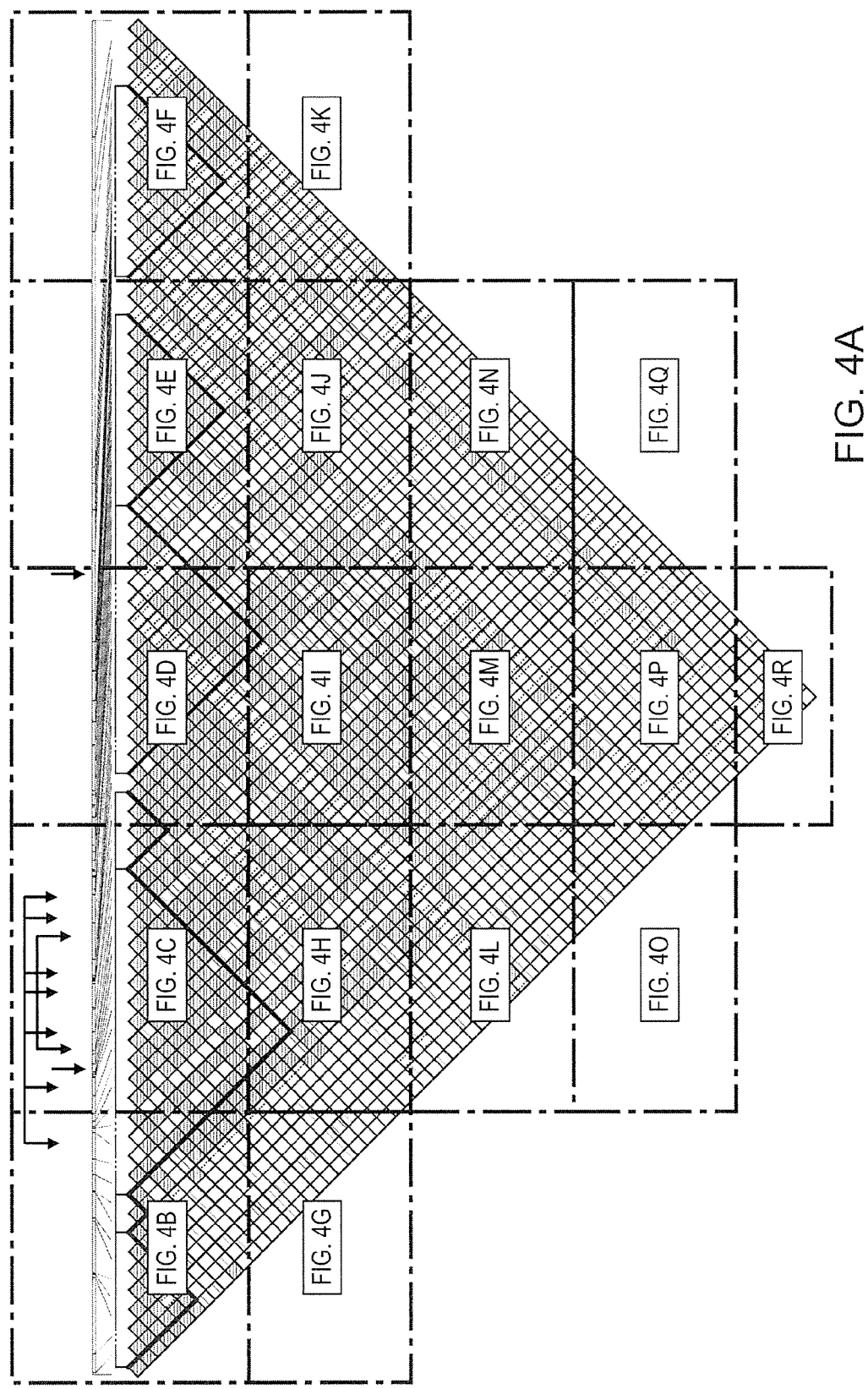
Figure 4B:
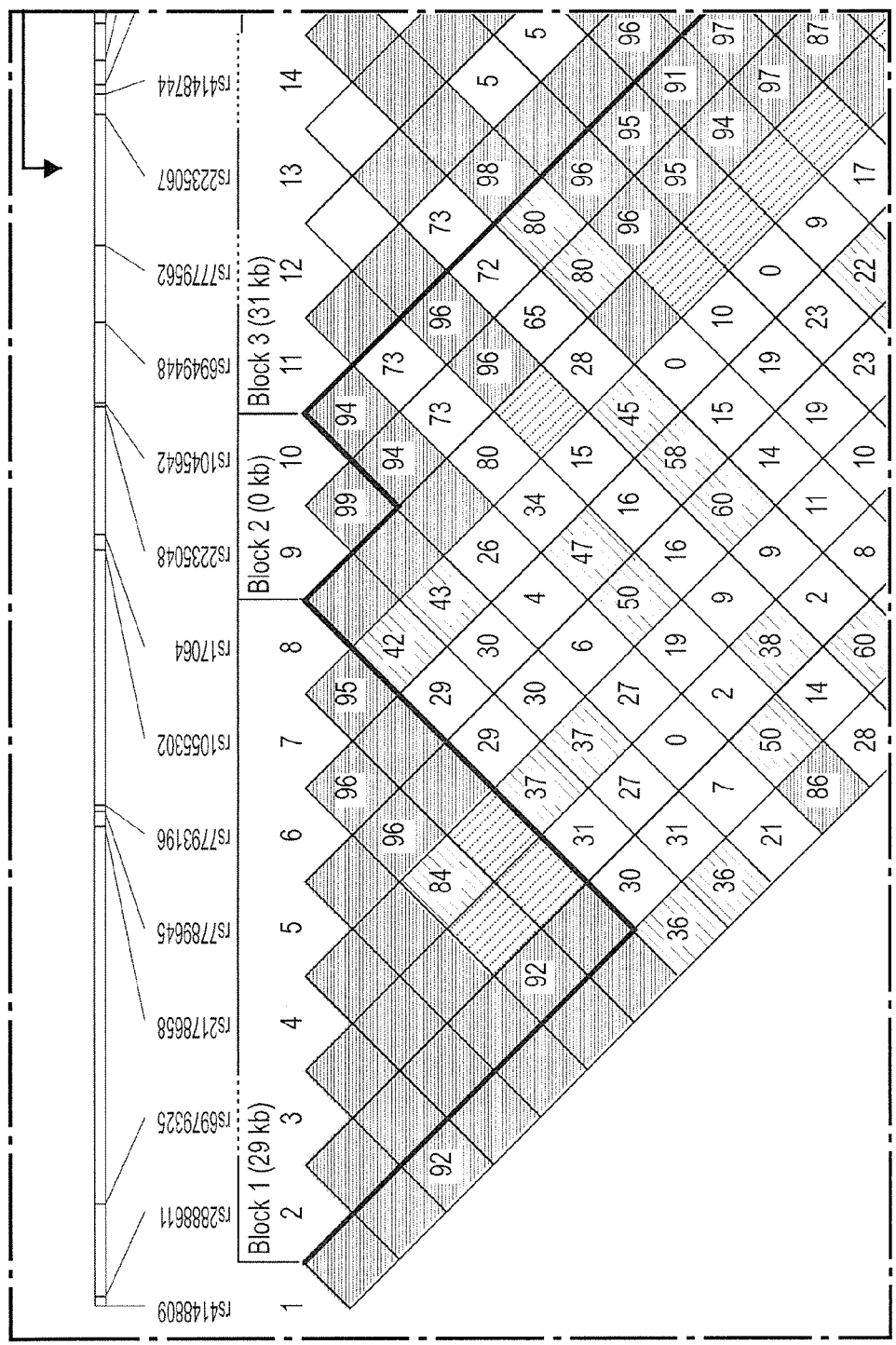
Figure 4C:
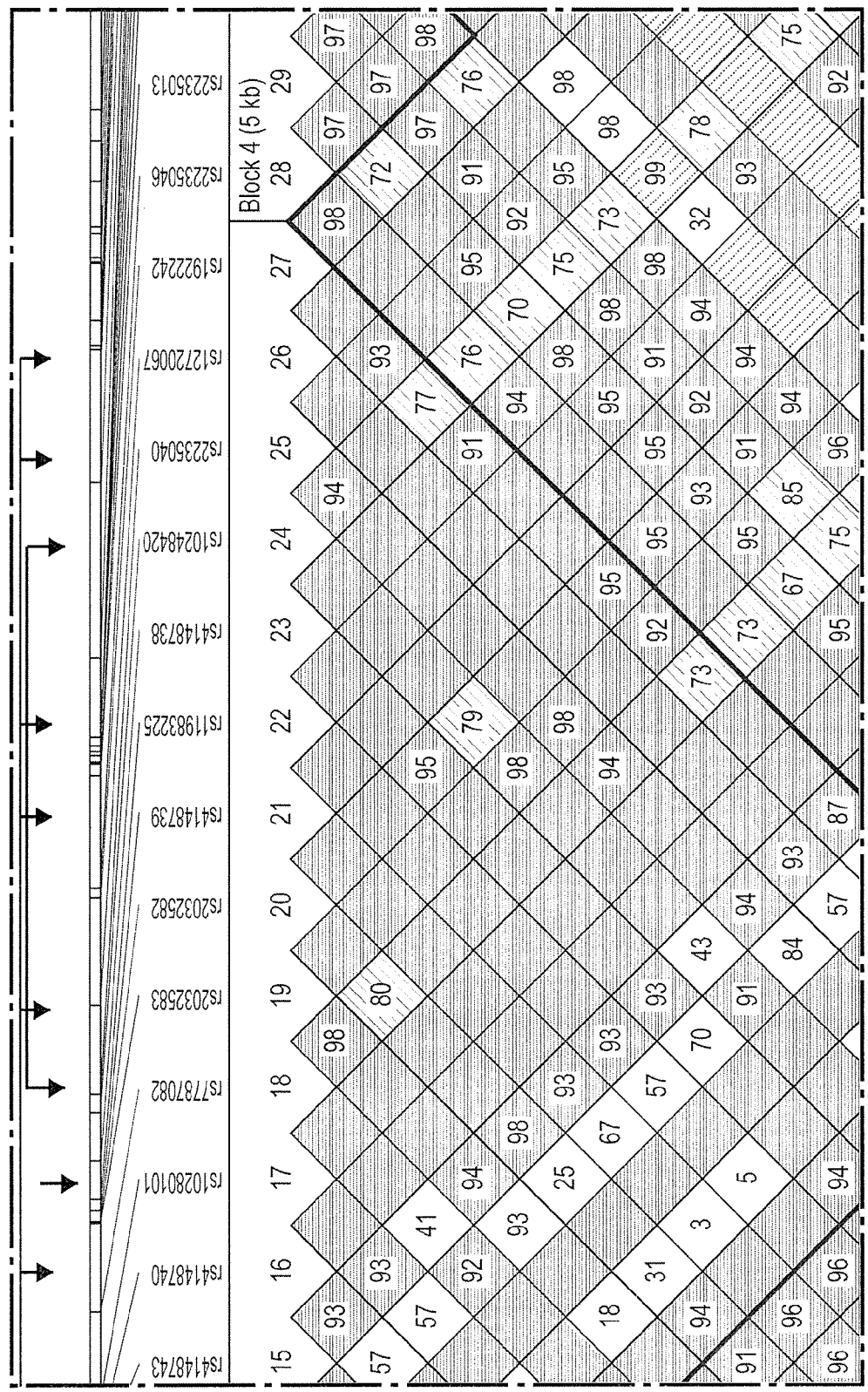
Figure 4D:
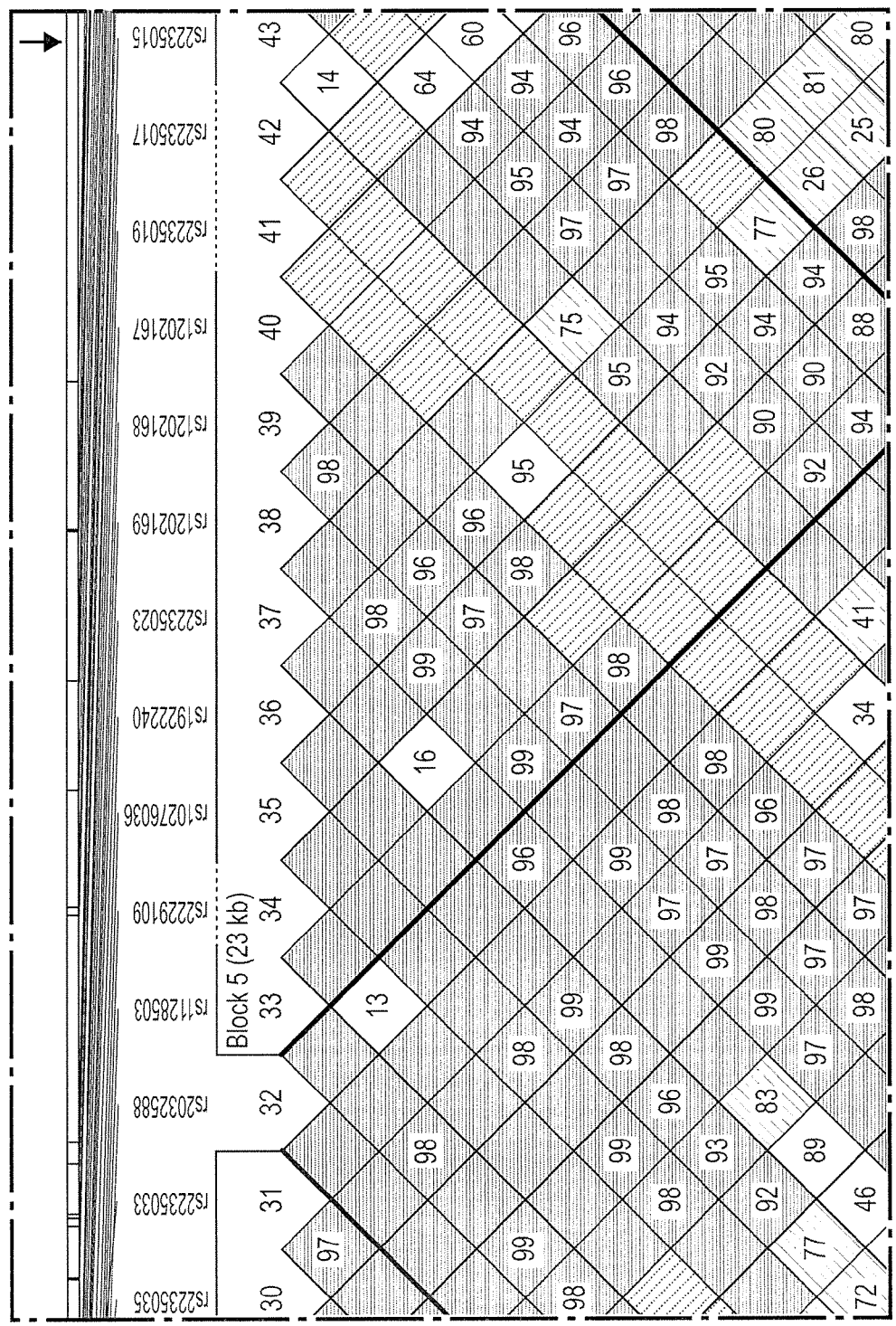
Figure 4E:
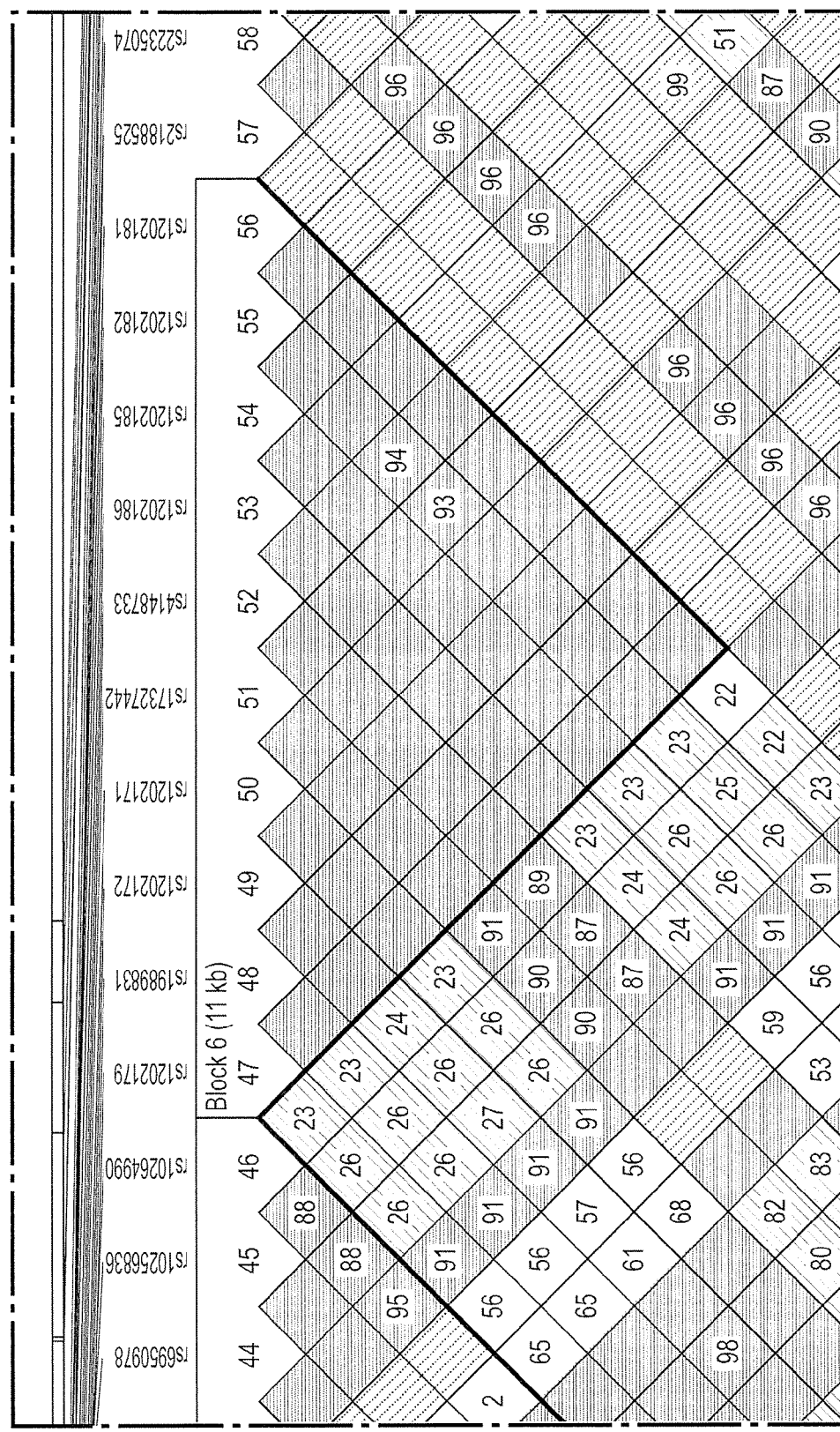
Figure 4F:
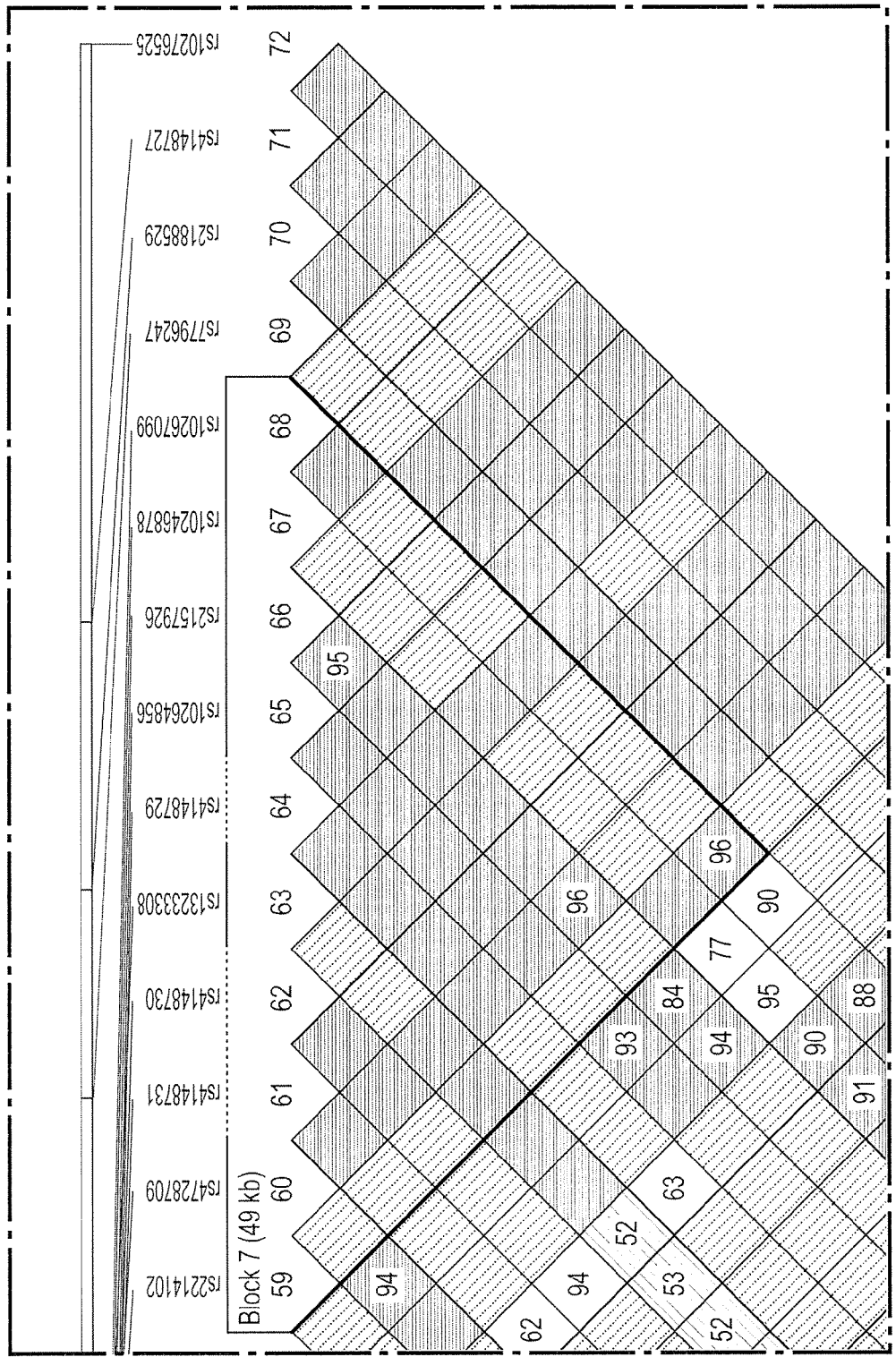
Figure 4G:
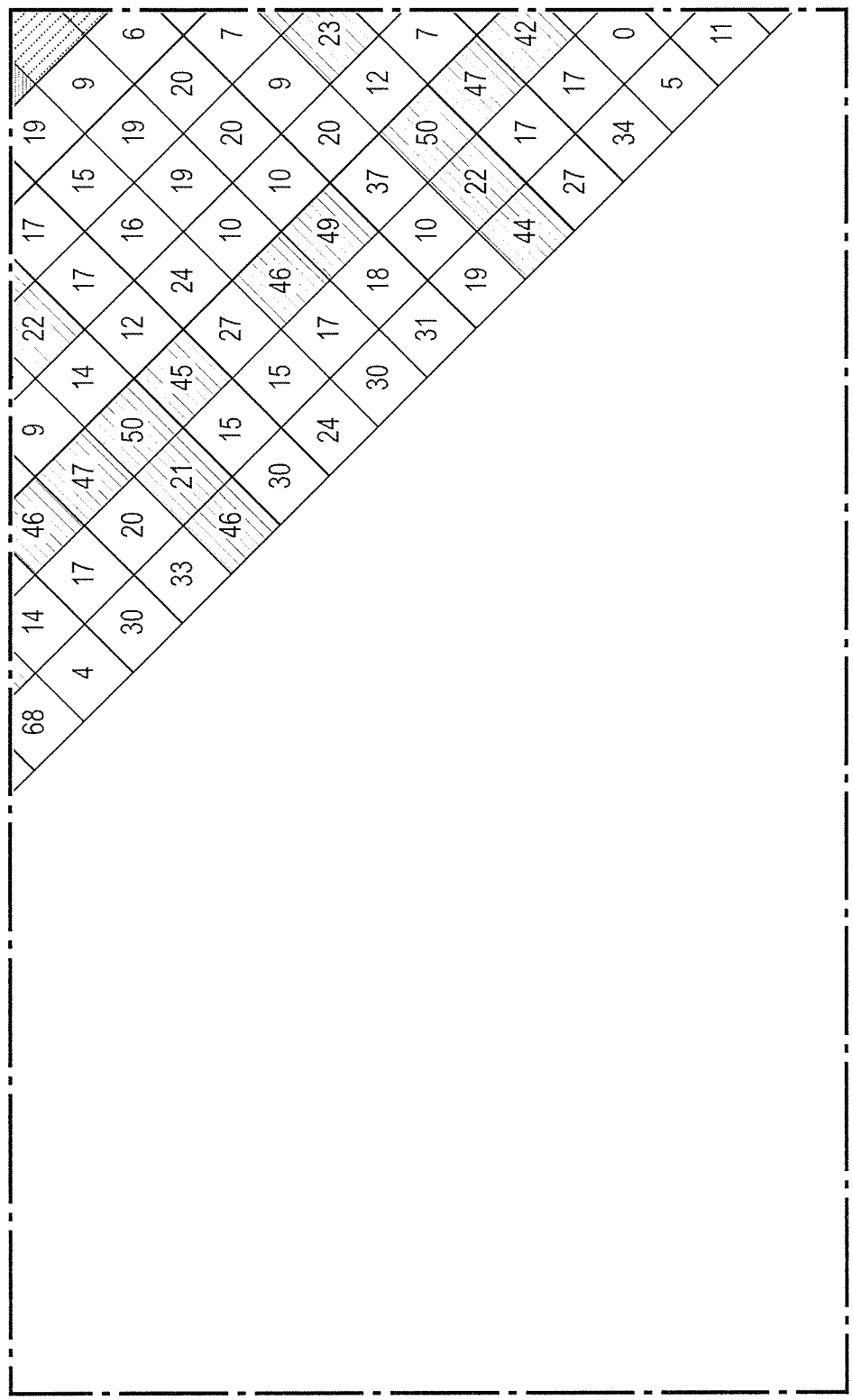
Figure 4H:
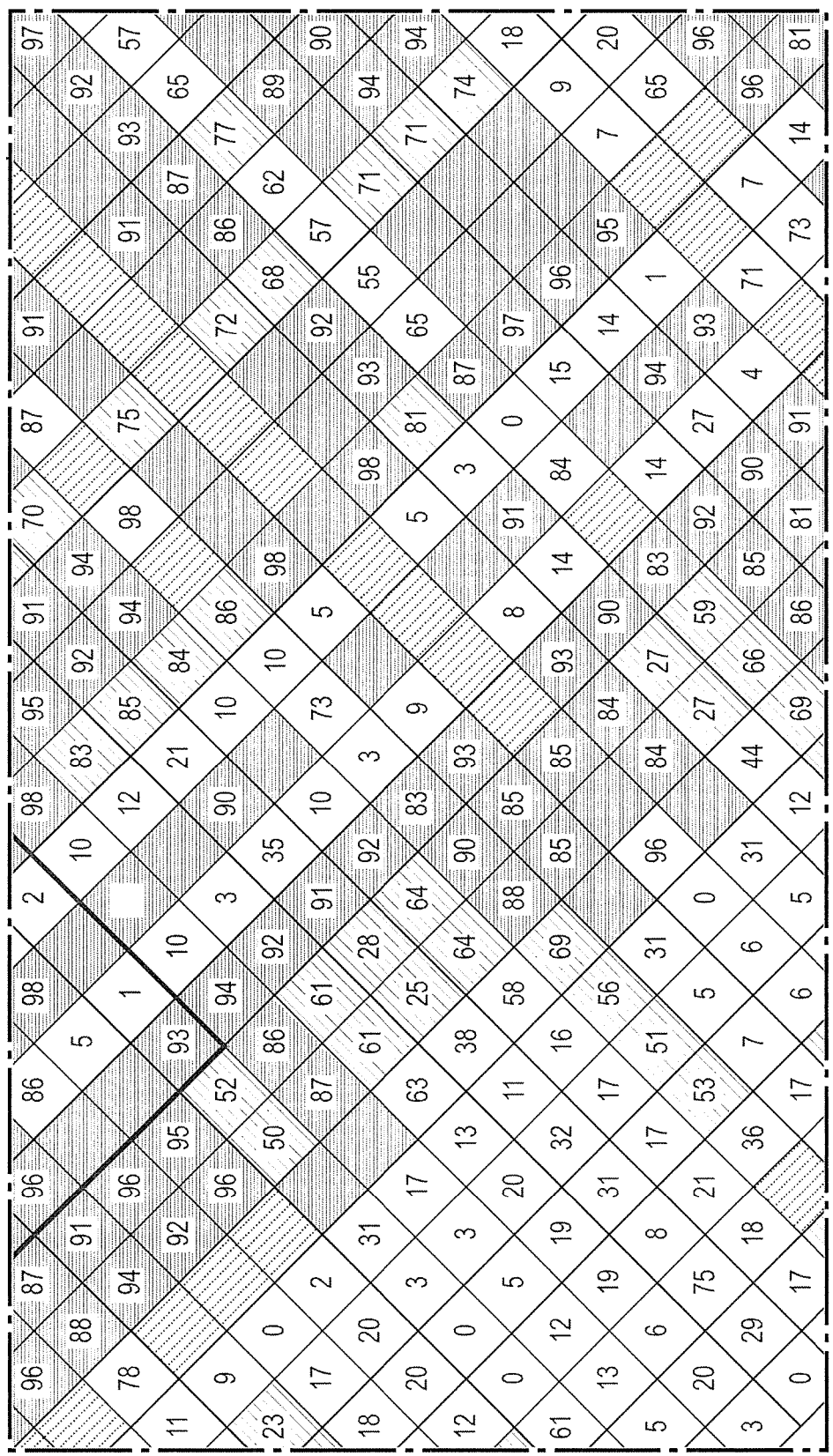
Figure 41:
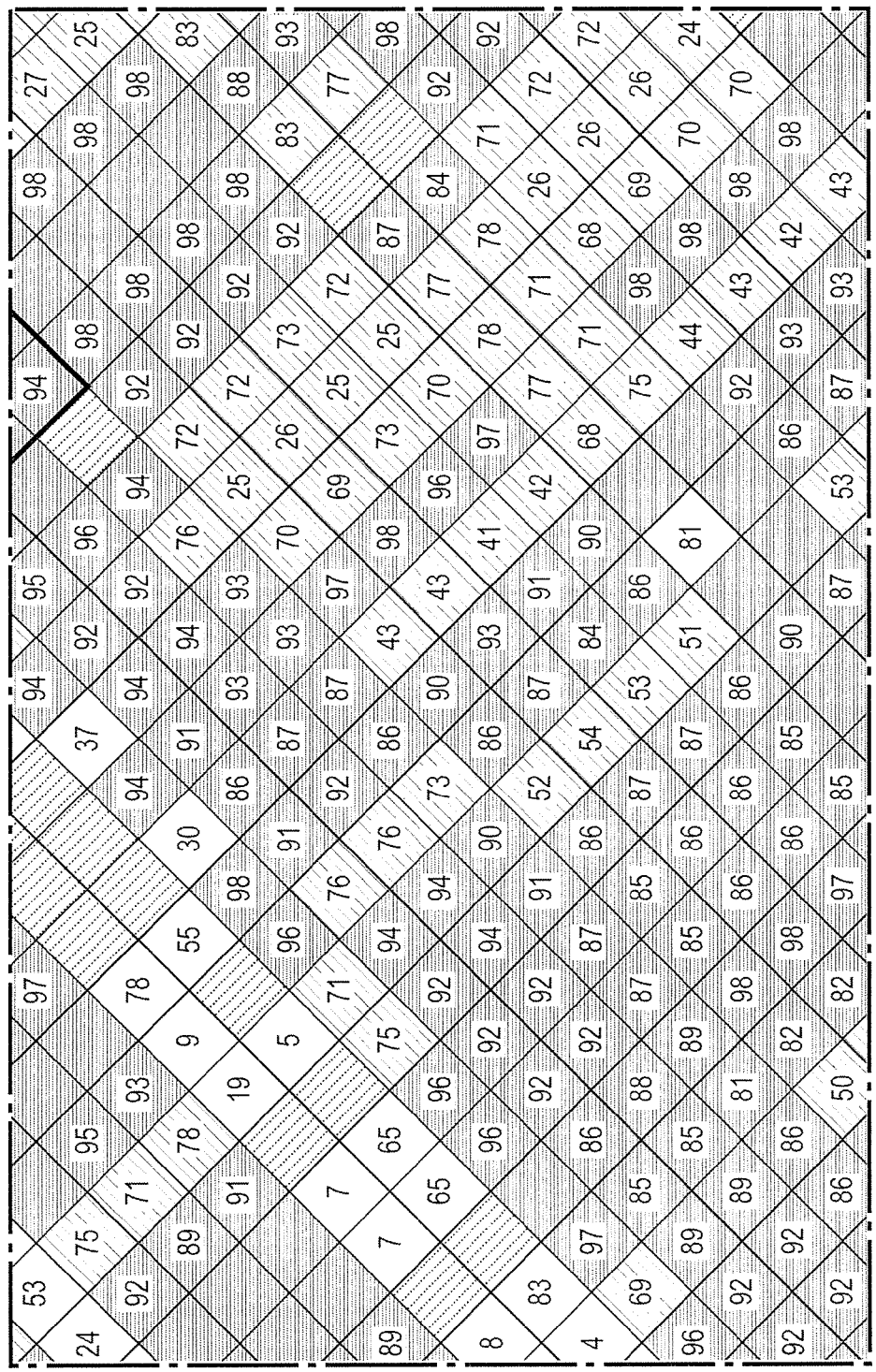
Figure 4J:
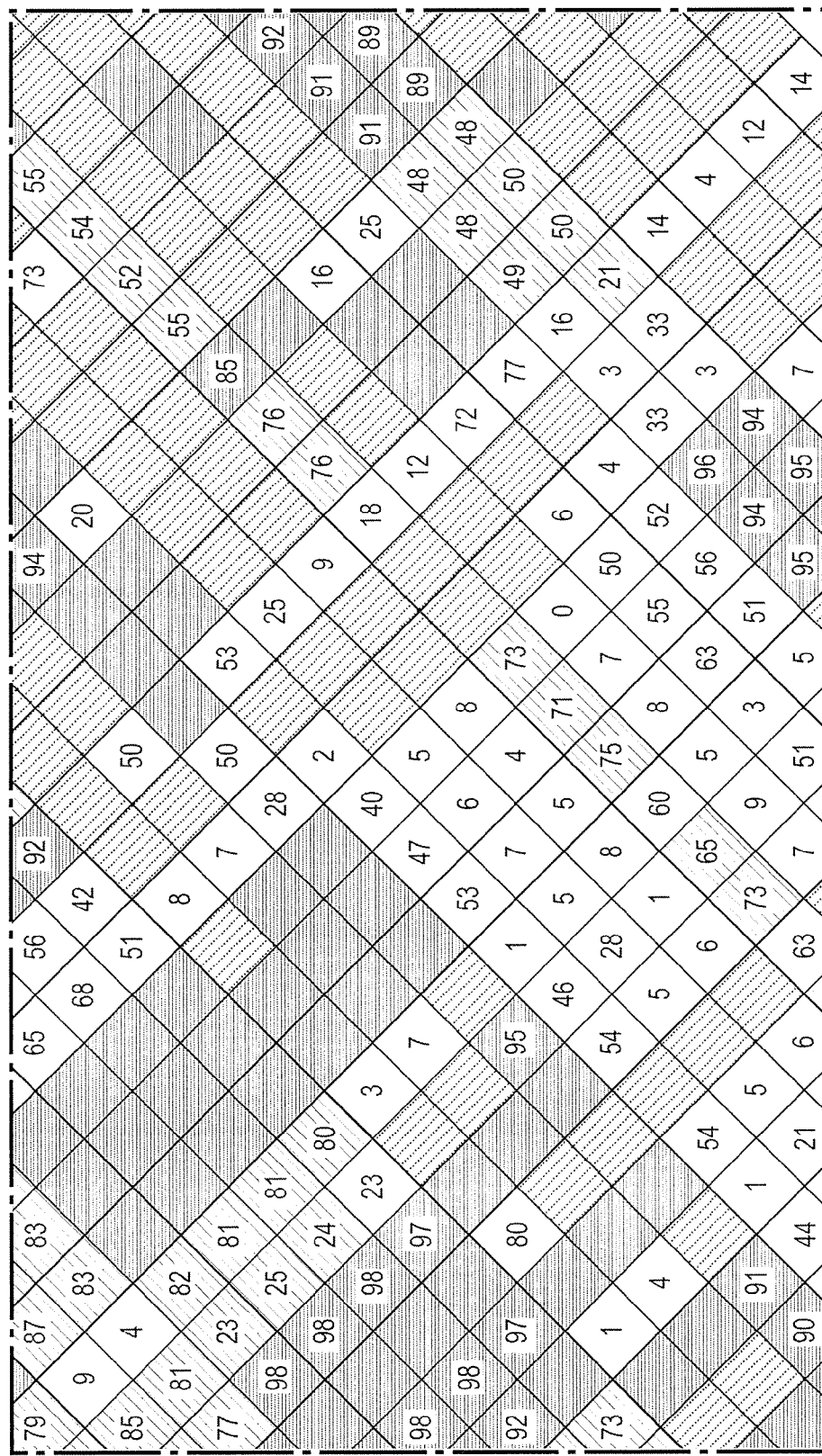
Figure 4K:
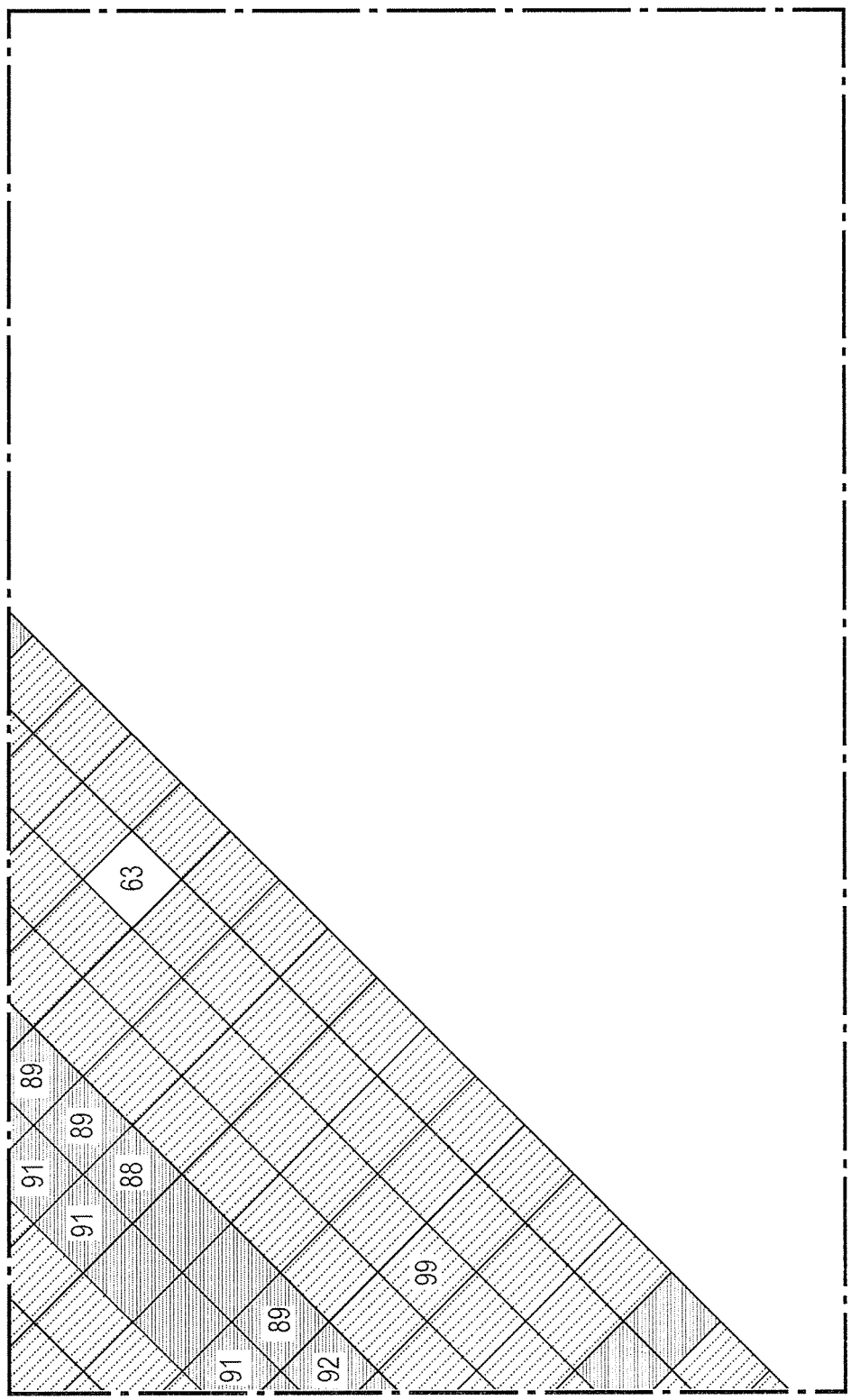
Figure 4L:
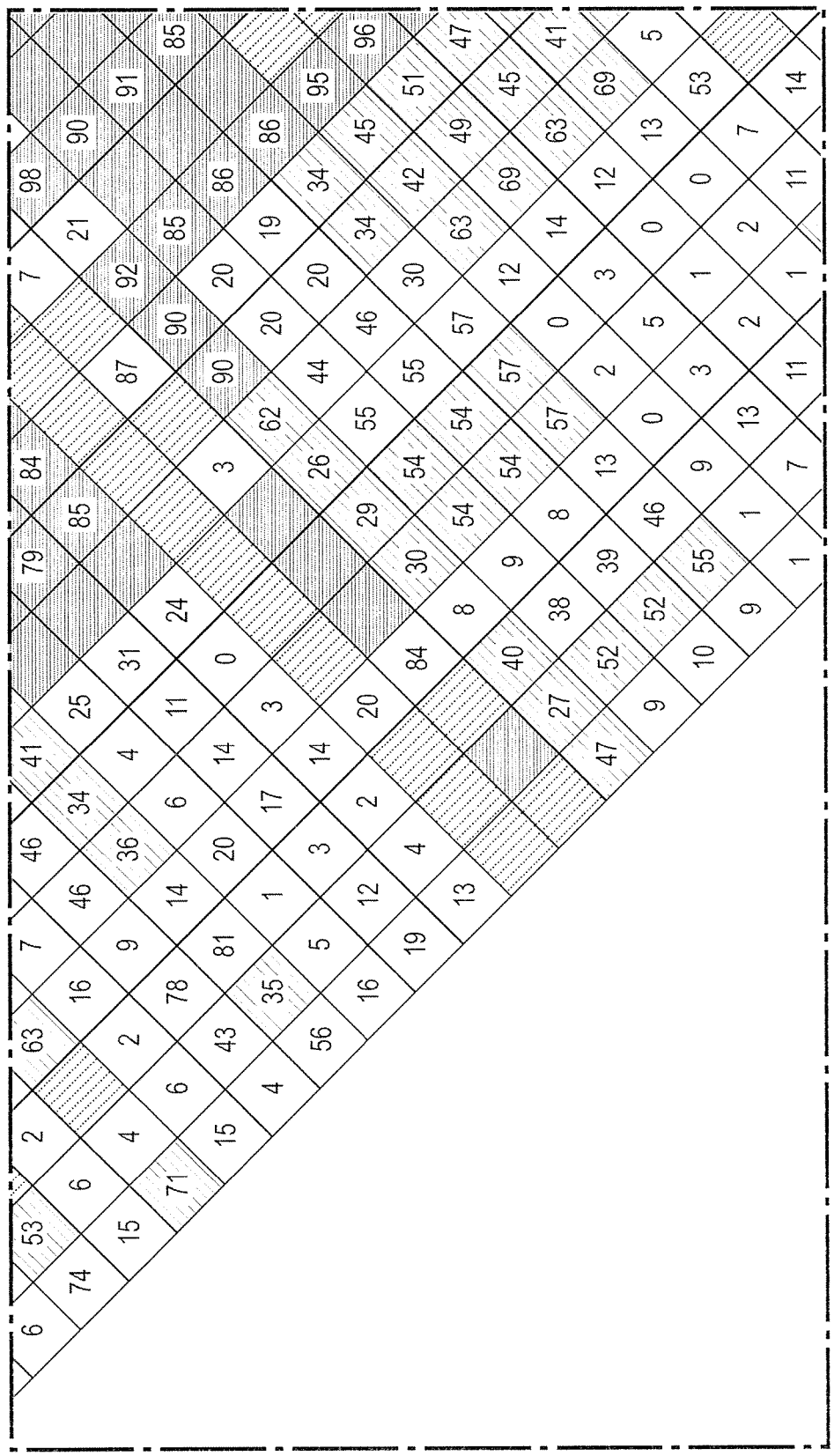
Figure 4M:
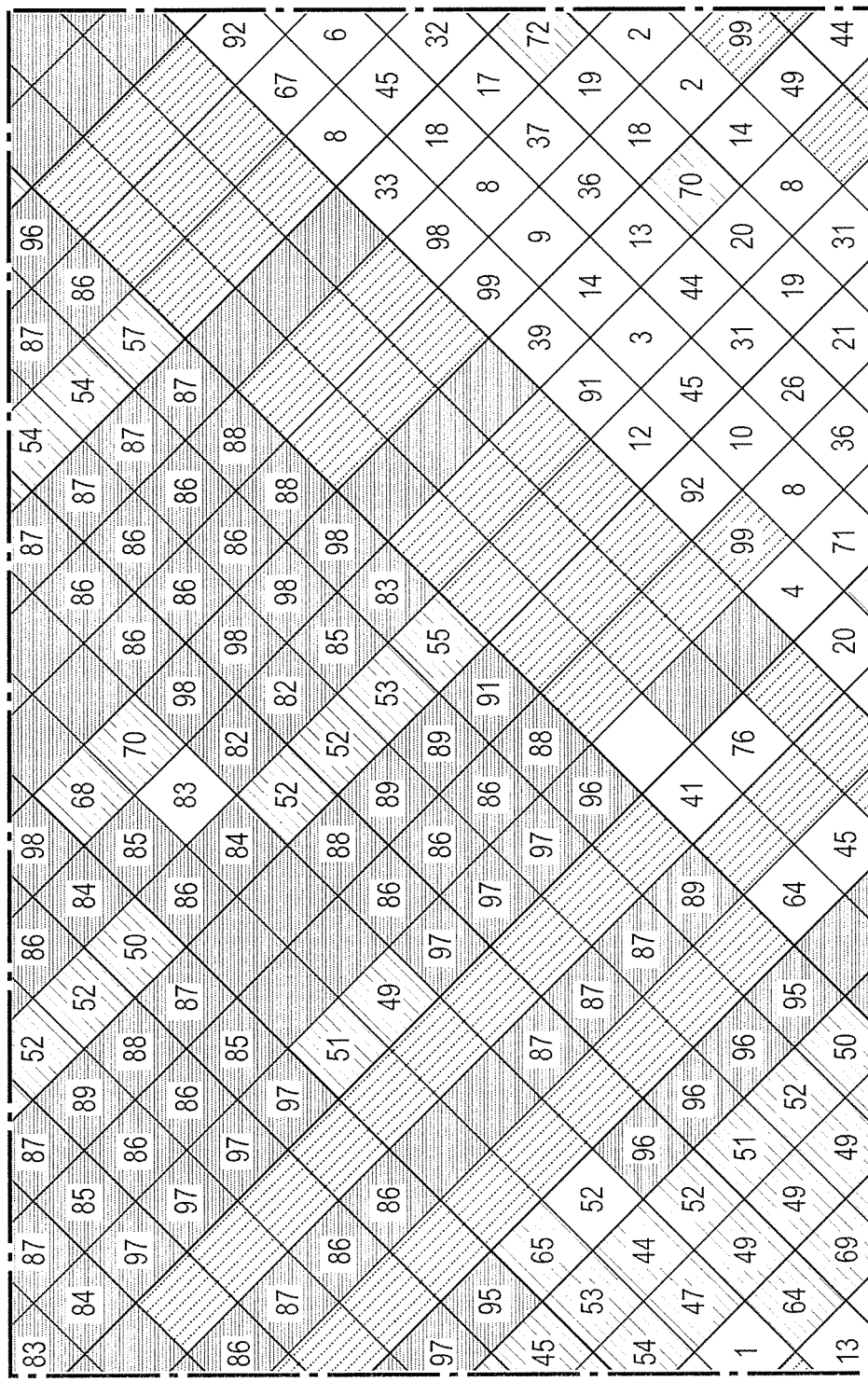
Figure 4N:
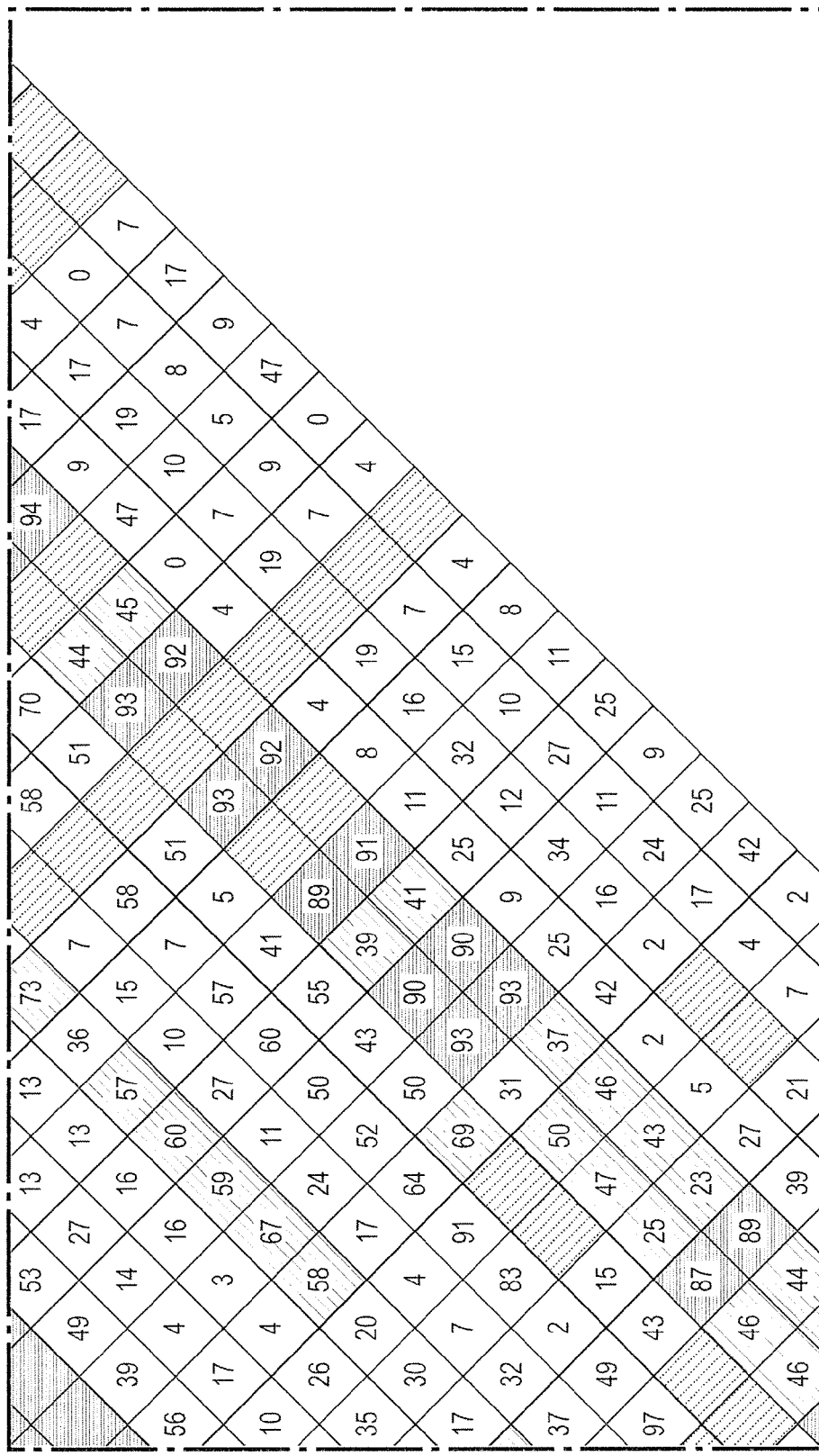
Figure 40:
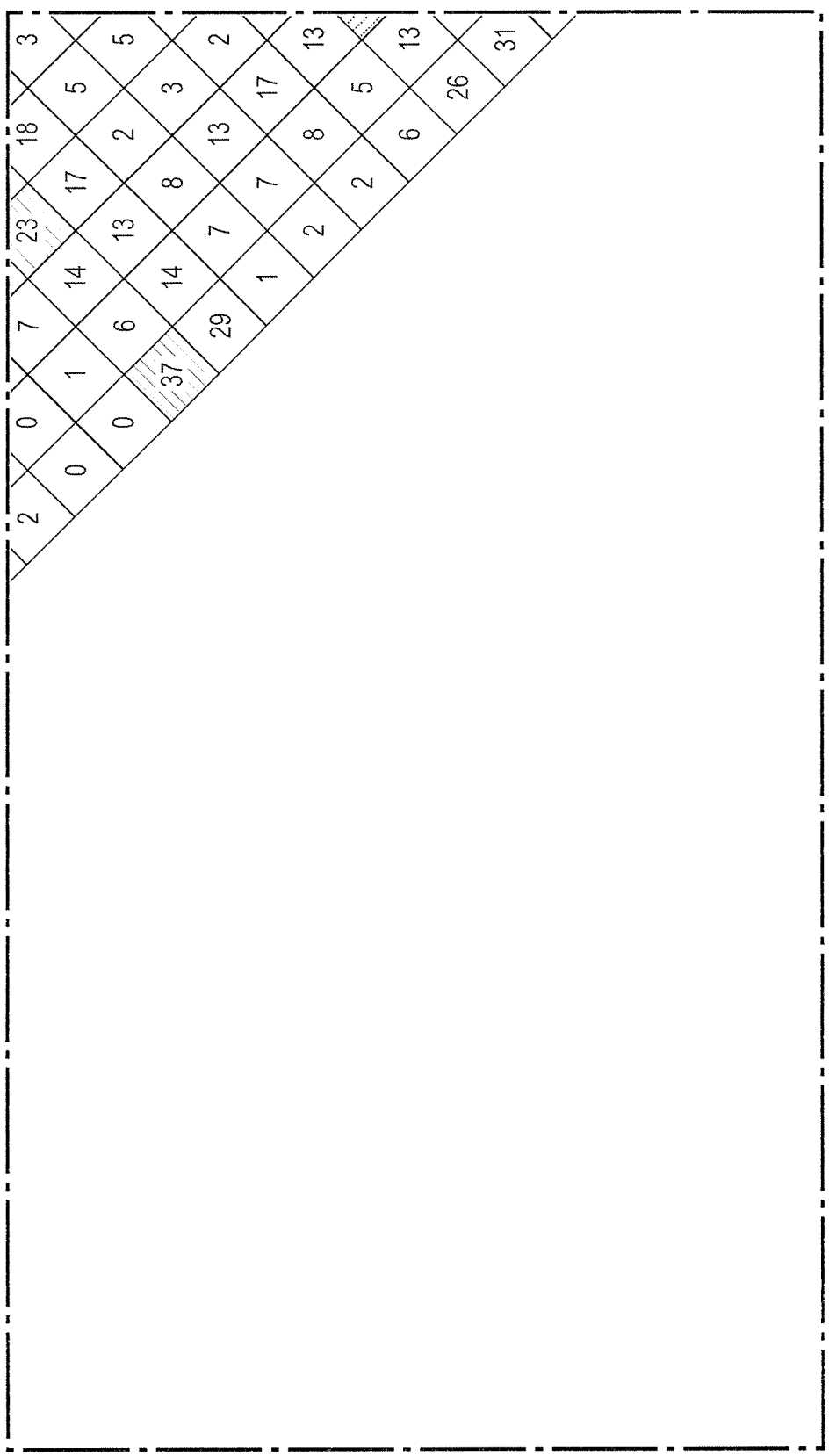
Figure 4P:
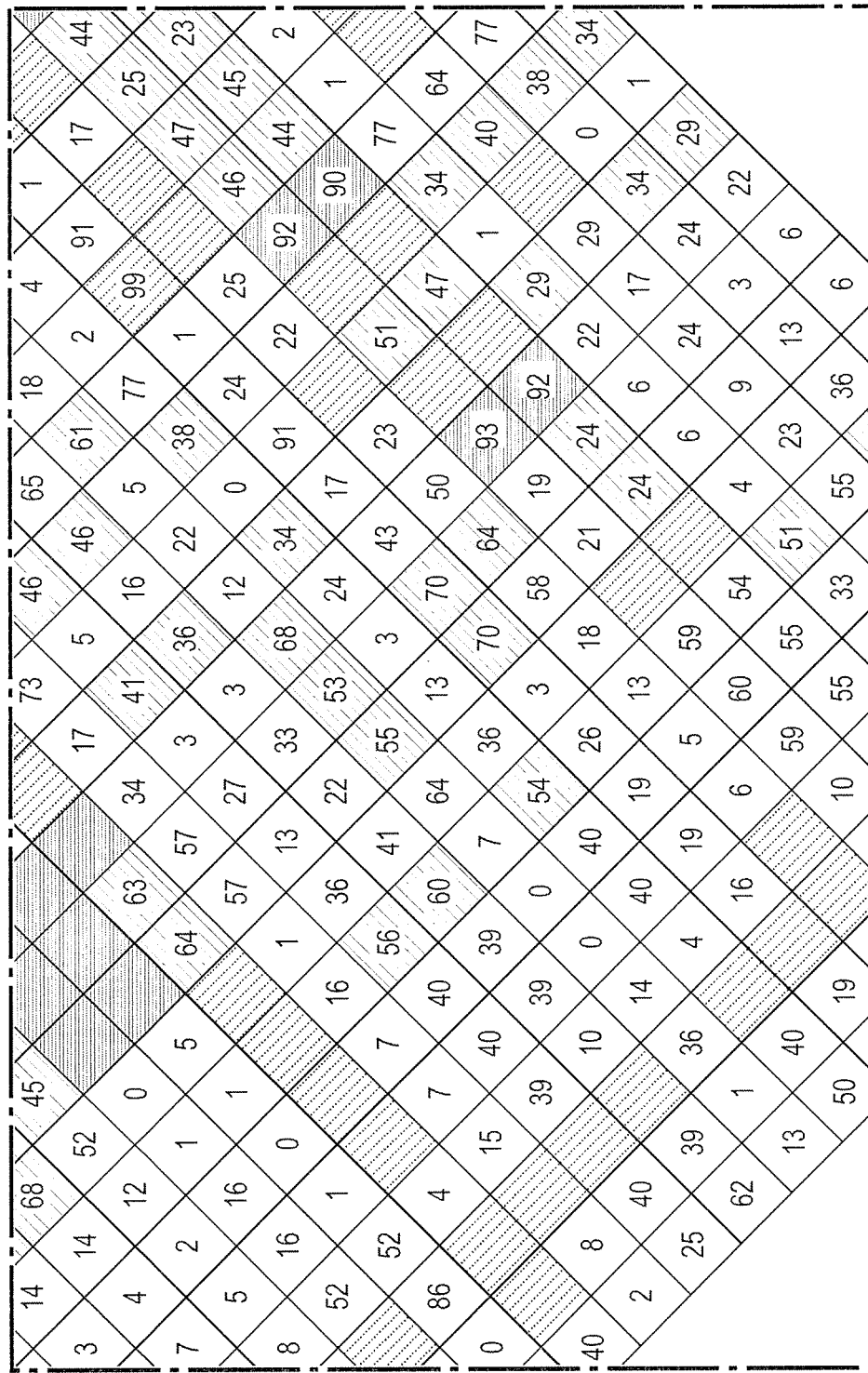
Figure 4Q:
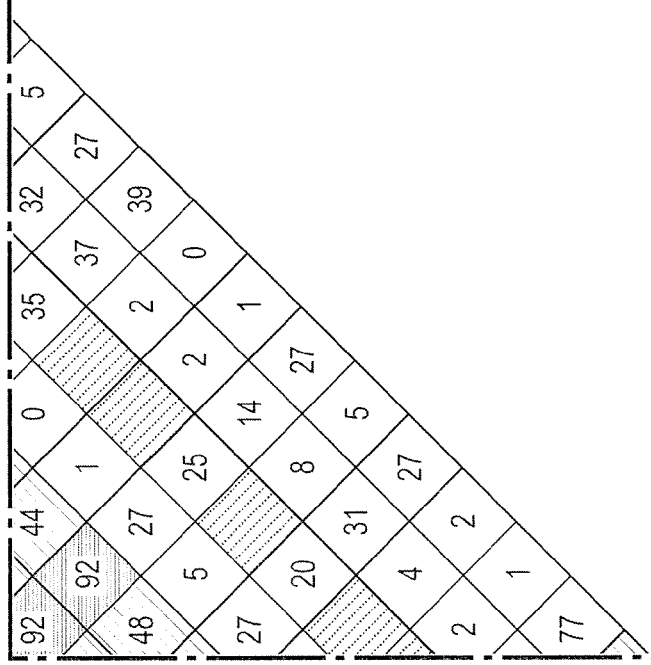
Figure 4R:
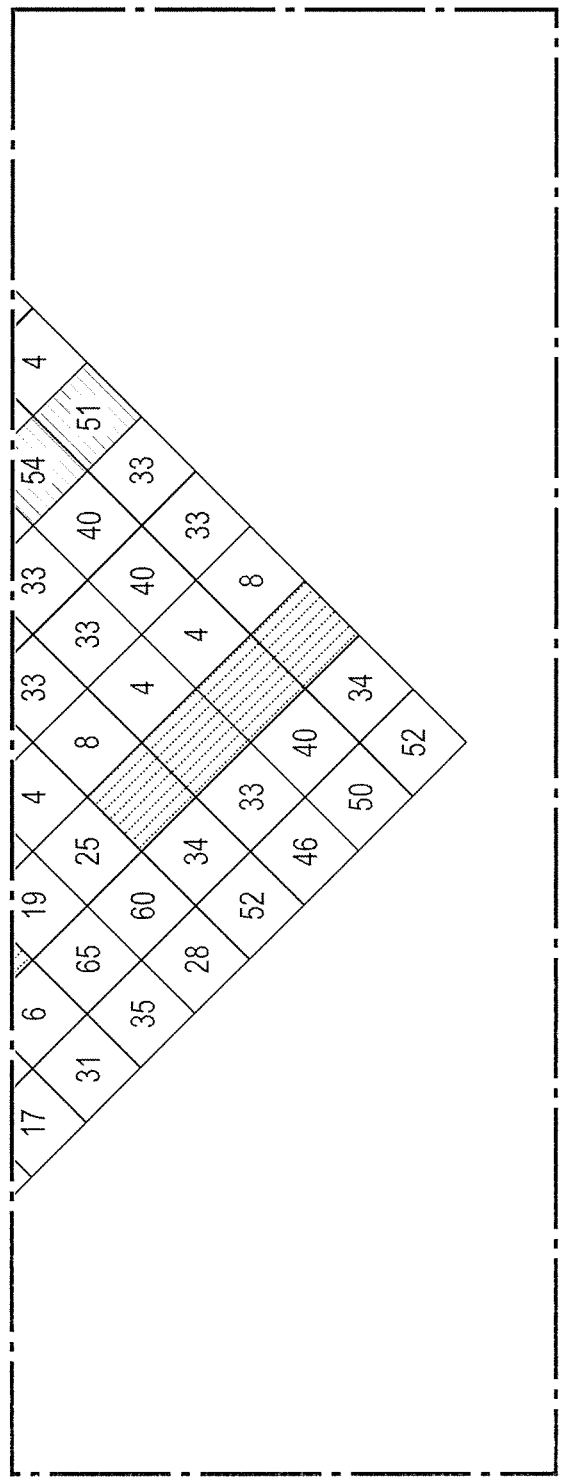

FIGS. 4A-R Linkage disequilibrium mapping

Representation of linkage disequilibrium (LD) and block structure in ABCB1 using D' as a measure for LD strength by means of HAPLOVIEW.

1. METHODS 1.1. Experiments Using Transgenic Animals

Materials.

Venlafaxine and O-desmethyl venlafaxine (d-venlafaxine) were obtained from Wyeth-Pharma GmbH (Munster, Germany). Mirtazapine was obtained from Thiemann Arzneimittel GmbH (Waltrop, Germany) and citalopram from Lundbeck (Copenhagen, Denmark). Protriptyline was purchased from Research Biochemical International, Natick, Mass. (USA). All other chemicals were obtained in the purest grade available from Merck (Darmstadt, Germany).

Animals.

All animal experiments were conducted in accordance with the Guide for the Care and Use of Laboratory Animals of the Government of Bavaria, Germany.

Male abcb1ab(−/−) mice and FVB/N wild-type mice were housed individually and maintained on a 12:12 h light/dark cycle (lights on at 07:00), with food and water ad libitum. Abcb1ab double knockout mice, originally created by A. Schinkel by sequential gene targeting in 129/Ola E14 embryonic stem cells (Schinkel et al., 1997) and back-crossed seven times (N7) to FVB/N from the C57BL/6×129 chimera, and FVB/N wild-type mice were obtained from Taconic (Germantown, N.Y., USA; FVB/Tac-[KO]Pgy2 N7). A homozygous colony is maintained at the Max Planck Institute of Psychiatry on the N7 FVB/N background through intercrossing of homozygous mice. Age, weight and group size of the mice used are shown in Table 9.

Experimental and Extraction Procedures.

Experimental and extraction procedures were performed as described before (Uhr et al., 2003; Uhr and Grauer, 2003). Citalopram, mirtazapine and venlafaxine dissolved in 0.9 percent sodium chloride and 0.5 percent ethanol were administered subcutaneously in the nape of the neck through surgically implanted osmotic infusion pumps (Alzet® micro-osmotic pump, Alza Corporation, Palo Alto, Calif., USA), which continuously delivered the drugs at the scheduled concentrations (citalopram and mirtazapine 60 µg/d; venlafaxine 300 µg/d). After 11 days, the mice were anesthetized and sacrificed. The dissected organs were homogenized and a liquid-liquid extraction procedure was performed with n-hexane/isoamyl alcohol in step 1 (see Table 9) and phosphoric acid in step 2. The extraction recoveries were greater than 90 percent for citalopram, mirtazapine and venlafaxine and 36 percent for d-venlafaxine.

High-performance liquid chromatography (HPLC) measurements were performed as described before (van de Vrie et al., 1998; Uhr et al., 2003). A Beckman gradient pump, an autoinjector, a UV detector and a Merck fluorescence detector were used for the HPLC analysis. Separations were made on a reversed phase Luna 5µ C18(2) 250×4.6 mm column (Phenomenex, Torrance, Calif., USA) at 60° C., with a mobile phase flow of 1 ml/min. A mobile phase gradient with acetonitrile was used for chromatographic analysis (see Table 9). The substances were determined by UV absorption and fluorescence.

Statistics.

Statistical analysis was performed using the statistic package software SPSS Release 14.0 for Windows (Chicago, Ill., USA). Significance was tested by one-factorial multivariate analyses of variance (MANOVAs). Univariate F-tests followed to identify the variables the differences of which between the two groups contributed significantly to the global group effect. As a nominal level of significance $\alpha=0.05$ was accepted and corrected (reduced according to the Bonferroni procedure) for all a posteriori tests (univariate F-tests) to keep the type I error less than or equal to 0.05.

1.2. Human Genetic Studies

Description of Patients.

The study included 443 in-patients with depressive disorder who were treated at the Max Planck Institute of Psychiatry (MPI), Munich/Germany. Patients were included in this study within 1-3 days of admission and diagnosed by trained psychiatrists according to the Diagnostic and Statistical Manual of Mental Disorders (DSM) IV criteria. Patients with depressive disorder due to a medical or neurological condition were excluded. Ethnicity was recorded using a self-report sheet for nationality, native language and ethnicity of the subject and of all 4 grandparents. The study was approved by the local ethics committee and written informed consent obtained from all subjects.

The study was designed as a naturalistic pharmacogenetic study (Munich Antidepressant Response Signature (MARS) project) (Künzel et al., 2003; Binder et al. 2004) designed to discover biomarkers and genotypes predictive of clinical outcome; all patients were treated according to doctor's choice of antidepressant drugs within a few days after admission. The antidepressant plasma concentration was monitored to assure clinically efficient drug levels.

The total group of patients was divided in two subgroups that differed from each other by the fact that the patients of both subgroups received drugs that were or were not substrates of P-glycoprotein in the animal model. In the group of patients taking antidepressants that are substrates of P-gp patients were taking amitriptyline, paroxetine, venlafaxine or citalopram for at least 4 weeks within the first 5 weeks of treatment. In addition, they were not allowed to take other antidepressants for more than 3 weeks (with the exception of trimipramine that was allowed in a daily dose of up to 100 mg for sleep promotion purposes). In the group of patients taking antidepressants that are not substrates of P-gp in the animal model patients had to take mirtazapine for at least 4 weeks within the first 5 weeks of treatment and were not allowed to take other antidepressants. If a patient was dismissed prior to week 5, he had to take the respective drugs for 3 weeks when hospitalized for 4 weeks and for 2 weeks in the case of a 3-week hospitalization. The group characteristics number of patients (% women), age, Hamilton Depression Rating Scale (HAM-D) at inclusion, age at onset, illness duration in years, number of previous episodes, number of former hospitalizations, duration of actual episode, ethnicity, co-medication and diagnosis are shown in Table 6 and Table 8, for the representative SNPs rs2032583 and rs2235015 depending on the genotype.

Not all patients finished the weekly psychopathology ratings until week 4 after being included in the study. After weeks 4, 5 and 6 the data of only 366 (83%), 324 (73%) and 297 (67%) patients were available for evaluation. This attrition was due to the patients' rapid recovery, discharge against their doctor's advice and relocation or refusal of further participation.

Psychopathology and Definition of Response to Antidepressant Drug Treatment.

Trained raters using the 21-item Hamilton Depression Rating Scale (HAM-D) assessed the severity of psychopathology at admission. Patients fulfilling the criteria for at least one moderate depressive episode (HAM-D>=14) entered the analysis. Ratings were performed within 3 days of admission and then weekly until discharge.

We defined response as a reduction of at least 50% in the HAM-D scores at admission. Remission was defined as reaching a total HAM-D score of less than 10. The 4 to 6 week time period was chosen because this duration of treatment is considered necessary for an antidepressant drug to display its clinical efficacy.

DNA Preparation, SNP Selection and Genotyping.

At the time of enrollment in the study, 40 ml of EDTA blood was drawn from each patient and DNA was extracted from fresh blood using the Puregene® whole blood DNA extraction kit (Gentra Systems, Minneapolis, Minn., USA). Ninety-five ABCB1 (NM_000927) SNPs were genotyped. SNPs were selected from dbSNP or part of the Illumina Sentrix Human-1 100 k BeadChips.

Genotyping was performed on a matrix-assisted laser desorption/ionization time-of-flight (MALDI-TOF) mass spectrometer (MassArray® system) employing the Spectrodesigner software (Sequenom®; San Diego, Calif., USA) for primer selection and multiplexing and the homogeneous mass extension (hMe) process for producing primer extension products. Cleaned extension products were analyzed by means of a mass spectrometer (Bruker Daltronik) and the peaks identified using the SpectroTYPER software (Sequenom). Only if the call rate of the plates tested was more than 90%, the results were used for evaluation.

SNPs that could not be examined by means of the Sequenom technology were tested by pyrosequencing (Biotage, Uppsala, Sweden).

rs7779562, rs4148738, rs2235033, rs10264856, rs10267099, rs7796247 and rs10275625 were performed on Sentrix Human-1 Genotyping BeadChips (Illumina Inc., San Diego, USA) according to the manufacturer's standard protocols. The SNPs rs2235048, rs1045642, rs2032583, rs2235046, rs1202169, rs2235015 and rs1202172 were performed using both the Sequenom and Illumina technology. The measuring results were congruent in more than 99%.

The tetra-allelic SNP rs2032582 was measured in the light-cycler using allele-specific hybridization probes. All primer sequences are available upon request.

Linkage Disequilibrium in ABCB1.

For the linkage disequilibrium (LD) structure examination D' and $r^2$ measures were used (Hill and Robertson, 1968). Analysis of measures was performed using HAPLO-VIEW Version 3.32. Blocks were defined using the confidence interval method described by Gabriel et al. (2002).

Statistics.

Exact tests to detect deviations from Hardy Weinberg equilibrium (HWE) (Wigginton et al., 2005) were performed for all SNPs (Table 2).

To calculate whether there exists a significant association between phenotype variables and genetic variability in the ABCB1 gene, the multivariate Fisher's product method (FPM) was employed. Phenotype variables were corrected for the effects of age and gender by calculating linear regression residuals with the statistic package software SPSS Release 14.0.0 (Chicago, Ill., USA). Bivariate associations between SNP genotyping data and phenotypes were tested in an ANOVA analysis (Analysis of Variance). Empiric p-values were calculated by applying $10^6$ permutations (phenotypes randomly redistributed over the genotypes). Fisher's product method (FPM) (Fisher, 1932) includes the residuals of the phenotype variables remission after 4 weeks, remission after 5 weeks, remission after 6 weeks, and the genotype variables from all polymorphic SNPs. P-value correction for multiple comparisons was done by re-sampling ($10^6$ permutations).

To correct for multiple testing, the permutation method by Westfall and Young (1993) was applied to take advantage of the dependence structure between the SNPs and the phenotypes. We performed the entire analysis scan $10^6$ times using phenotypes randomly redistributed over the genotypes. Finally, a Cox regression survival analysis was carried out with the statistic package software SPSS Release 14.0.0 (Chicago, Ill., USA), examining remission incidence (HAM-D<10) during the first 6 weeks of treatment, with age and sex as covariates.

Results

Experiments Using Abcb1a and Abcb1b Double Knockout Mice

Since P-gp function is only critical for drugs that are substrates of P-gp in humans, an in vivo assay was developed using mouse mutants lacking the homologues of the human ABCB1 gene, i.e. abcb1ab knockout mice. After treatment for 11 days with subcutaneously implanted osmotic infusion pumps it was observed that the intracerebral concentrations of the antidepressants citalopram ($F_{7,8}$=35.4; p<0.001), venlafaxine ($F_{7,8}$=30.7; p<0.001) and its active metabolite d-venlafaxine ($F_{7,8}$=4.5; p=0.022) are regulated by P-gp. The brain concentrations of citalopram, venlafaxine and d-venlafaxine were 3.0, 1.7 and 4.1 times higher in the mutant mice compared to their wild-type littermates (Table 2). This was not the case for mirtazapine, another frequently used antidepressant ($F_{8,9}$=3.0; p=0.58). No differences in plasma levels were found between abcb1ab (−/−) mutants and their wild-type littermates for any of the drugs and metabolites investigated (Table 2).

The blood-organ barrier function is represented in FIG. 1 as an organ/plasma concentration ratio. In the animals lacking P-gp, the penetration into the brain of citalopram, venlafaxine and d-venlafaxine is 3.7, 1.8 and 3.6 times higher than that found in the control animals. Beside differences in brain/plasma ratios smaller but still significant differences were found for citalopram, venlafaxine and d-venlafaxine, but not mirtazapine, in the testes, another organ with a blood-organ barrier.

Human SNP Association Study

If a patient is treated with a substrate of P-pg, functionally relevant genetic variants in the ABCB1 transporter could influence intracerebral drug concentrations and thereby clinical response. To test this hypothesis, the association of single nucleotide polymorphisms (SNPs) in the ABCB1 gene with the time until remission under antidepressant treatment was analysed in patients with depressive disorders.

To that aim 95 SNPs in ABCB1 were investigated, 74 of which were polymorphic. Information on chromosome position, function, HWE, minor allele frequencies (MAF) and the number of patients genotyped are presented in Table 7. The average intermarker distance of informative SNPs was 3.5 kb over the 262 kb long ABCB1 region on chromosome 7 including all tagging SNPs of the HapMap project.

Since P-g does not influence cerebral penetration of all antidepressants, patients were divided in two subgroups, one group including patients treated with substrates of P-gp (citalopram, paroxetine, amitriptyline and venlafaxine), the other one including patients treated with non-substrates (mirtazapine) (Uhr et al., 2000, 2003, 2007; Uhr and Grauer, 2003; Grauer and Uhr, 2004).

All polymorphic SNPs were tested for genotypic association with the phenotypes remission after 4 weeks, remission after 5 weeks or remission after 6 weeks.

Table 3 shows the empiric p-values of the ANOVA analysis determined by applying $10^6$ permutations and corrected for age and sex for both the entire group and the two subgroups.

An association with p-values of <0.001 was found only in the subgroup including patients who received drugs that were substrates of P-gp. The SNPs concerned were rs2235067, rs4148740, rs10280101, rs7787082, rs2032583, rs4148739, rs11983225, rs10248420, rs2235040, rs12720067 and rs2235015.

This association analysis for all polymorphic SNPs and phenotypes was conducted according to Fisher's product method (FPM) (Fisher, 1932) for the genotypic and allelic models. Correction for multiple testing was performed using the minimum P method of Westfall and Young (1993). Table 4 shows the p-values of FPM over all SNPs, sorted by phenotypes and models, as well as over all SNPs and all phenotypes, sorted by model and the Westfall-Young corrected p-values. In the group of patients taking substrates of P-gp there exist highly significant associations between the genetic variability of the SNPs tested and both the remission of depressive symptoms in weeks 4, 5 and 6 and the combination of these remission variables. In this group of patients the Westfall and Young corrected p-values over all SNPs and phenotypes was 0.00040 and 0.00016 for the genotypic and allelic analysis. In the group of patients taking drugs that are not substrates of P-gp there was no significant association.

This is illustrated in FIG. 2, which presents the genotype distribution of the SNP rs2032583 for patients who remitted after 4 weeks and those who did not. In the group of patients receiving antidepressants that are substrates of P-gp there are clear differences in the genotype distribution between remitters and non-remitters (FIG. 2A). While in the group of non-remitted to patients carrying the C-allele made up 9.5%, their percentage in the group of remitted patients was 45%. The 2×3 table Cochran-Armitage test yielded a chi-square of 15.8, p=0.00007 for patients receiving the P-gp substrates and a chi-square of 0.004, p=0.945 for patients receiving a non-P-gp substrate. If C-carriers are treated with drugs that are substrates of P-gp, they have a clearly higher approx. relative risk for remission after 4 weeks. The odds ratio (approx. relative risk) was 7.72 (95% confidence interval limits 2.80 and 21.32) with p=0.000065 in the 2×2 table Fisher's exact test. For any particular negative test result (non-carrier), the probability that it was true-negative (non-remission) was 81.5%.

For patients receiving non-P-gp substrates there are no differences in the genotype distribution between remitters and non-remitters (FIG. 2B). The odds ratio was 1.12 (95% confidence interval limits 0.38 and 3.37) with p=1 in Fisher's exact test.

For a better presentation of the remission development up to week 6 a survival analysis (Cox regression) was performed. FIG. 3 shows the decrease in non-remitters, i.e. patients who are still ill, for all patients and the two subgroups during the first 6 weeks depending on their genotype. For rs2032583 a distinction was made between C-carriers and non-carriers; for rs 2235015 we distinguished between T carriers and non-carriers. The group of patients treated with a substrate of P-gp shows clear differences depending on the genotype. For instance, after 6 weeks, 62% of the patients who are non-C-carriers of the SNP rs2032583 had not remitted, while this was the case in only 25% of the C-carriers.

For all SNPs showing a highly significant association between genotype and remission in the FPM a Cox regression was performed; the values of the Wald statistics and p-values are shown in Table 5. In the group of patients who had received drugs that are substrates of P-gp there was a significant difference for all SNPs tested (p-values <0.0025). The subgroup of patients taking an antidepressant where its brain concentrations are not influenced by P-gp did not show any differences.

Linkage Disequilibrium in ABM

In an attempt to narrow down the region of ABCB1 containing the causal variant, the linkage disequilibrium (LD) structure of ABCB1 was analyzed using HAPLO-VIEW. This analysis included all patients. Applying the method of Gabriel et al. (2002) for the delineation of haplotype blocks, a total of 7 blocks were identified (FIG. 4).

The 11 SNPs that showed a highly significant association between genotype and remission in the FPM are marked with an arrow. The linked SNPs rs2235067, rs4148740, rs2032583, rs4148739, rs11983225, s2235040, rs12720067 as well as the SNPs rs7787082 and rs10248420 exhibited an r-square of >0.8. The SNPs rs10280101 and rs2235015 were not included in any tagging bin with an r-square of >0.8.

Genotype, Plasma Antidepressant Levels and Dosage

To exclude the possibility that the observed effect is based solely on differences in the administered drug dose or intestinal uptake, and to support the hypothesis that genotype-related differences in treatment response are linked to differences in intracerebral drug concentrations, we examined whether there were significant differences in the doses and plasma levels of amitriptyline, citalopram, paroxetine, venlafaxine and mirtazapine between the genotypes of significant SNPs.

To this end, we created the residuals of linear regression with the dependent variable drug dose or plasma concentration and the independent variables age and gender. These residuals and SNP genotyping data were tested in an ANOVA analysis for statistical differences between the genotypes. Empiric p-values were calculated by applying $10^6$ permutations (residuals randomly redistributed over the genotypes). Fisher's product method (FPM) includes the residuals of the dose or plasma concentration variables and the genotype variables from the SNPs rs2235067, rs4148740, rs2032583, rs4148739, rs11983225, rs2235040, rs12720067, rs7787082, rs10248420, rs10280101 and rs2235015.

We neither found significant differences in the doses of amitriptyline, citalopram, paroxetine, venlafaxine and mirtazapine between the SNP genotypes studied nor genotype-dependent differences in the plasma levels of patients receiving amitriptyline, paroxetine, venlafaxine or mirtazapine. However, a small significant difference could be detected for citalopram plasma levels. Although Fisher's product over all SNPs and phenotypes was p=0.023 for the genotypes, the plasma levels of patients showing less treatment success was higher.

Case-Control Association

A control group of 362 subjects was genotyped for rs2032583 and rs2235015, the representative SNPs in the haplotype blocks 3 and 5 in the LD map (FIG. 4). Subjects were randomly selected from a Munich-based community sample and were negative for lifetime psychiatric axis I disorders (M-CIDI) and severe somatic diseases. Controls did not differ from the patient sample regarding gender distribution (p=0.603), age (p=0.322) or ethnicity (100% Caucasians in both samples, p=1). Genotype tests were performed using Fisher's exact test on a 2×3 table. We observed no significant case-control association for rs2032583 and rs2235015 (Fisher's exact test, p=0.669 and 0.351).

DISCUSSION

The present results provide for the first time evidence that genetic variants in the ABCB1 gene account for differences in the clinical efficacy of antidepressants most likely by influencing their access to the brain. Here it is reported that antidepressant-induced remission of depressive symptoms is predicted by SNPs in the ABCB1 gene among those depressed patients who were treated with drugs that are substrates of the ABCB1-encoded P-glycoprotein. To identify whether or not the antidepressants administered to patients are substrates of the P-glycoprotein, mouse mutants lacking the mouse homologues of the ABCB1 gene were studied. Whereas P-gp is encoded by a single gene in humans (ABCB1), there are two homologues in mice, the abcb1a and abcb1b genes (Devault and Gros, 1990). Although abcb1a and abcb1b are not always expressed in the same organs, the overall distribution of these genes in mouse tissue coincides with that of the single ABCB1 gene in humans, indicating that abcb1a and abcb1b together function in the same manner in mice as human ABCB1 (Meijer et al., 1998; van de Vrie et al., 1998). It has yet not been possible to predict the affinity of a substrate to P-glycoprotein from its chemical structure, hydrophobicity, lipophilicity or charge. Using this mouse model, it could already be shown in earlier studies that citalopram, venlafaxine, paroxetine and amitriptyline, after single administration, were substrates of P-gp at the blood-brain barrier, while mirtazapine and fluoxetin were not (Uhr et al., 2000, 2003, 2007; Uhr and Grauer, 2003; Grauer and Uhr, 2004).

In this study, the drugs were administered over an extended time period to investigate the time-dependent interaction of the drug and P-gp. It is shown that two structurally different antidepressants citalopram (a selective serotonin reuptake inhibitor) and venlafaxine (a combined serotonin and norepinephrine reuptake inhibitor) were both substrates of P-gp at the BBB as the brain drug concentration in mutants not carrying the genes coding for P-gp was increased (Table 2, FIG. 1). In contrast, the penetration of mirtazapine (targeting serotonin2C and alpha2A-adrenergic receptors) into the brain is not influenced by P-gp. The important role of P-gp was further supported by the fact that drug and metabolite organ concentrations and organ/plasma ratios of all antidepressants investigated did not differ between mutant and wild-type littermates in those organs that either lack P-gp completely or in which P-gp is not expressed in endothelial cells, such as the spleen, kidney, liver and lung. These results shows that some but not all antidepressants are substrates of P-gp in mice. In this study the antidepressants were administered for 11 days and it was found that the substrate specificity is similar to that observed after acute administration (Uhr et al., 2000, 2003; Uhr and Grauer, 2003), indicating that P-gp substrate specificity or activity does not change over time.

To answer the question whether differences in the access of antidepressants into the brain might influence the course of treatment and outcome, a clinical study was conducted in which the genetic variability of the ABCB1 gene of 443 in-patients with depressive disorder receiving antidepressants was investigated. Patients were divided in two groups, those receiving drugs that had proved to be substrates of P-gp at the BBB (amitriptyline, citalopram, paroxetine and venlafaxine) and those receiving mirtazapine, which is not a substrate.

Numerous papers describe polymorphisms in ABCB1 (Kioka et al., 1989; Stein et al., 1994; Mickley et al., 1998; Hoffmeyer et al., 2000; Kim et al., 2001; Ito et al., 2001; Cascorbi et al., 2001; Tanabe et al., 2001; Eichelbaum et al., 2004), and a multitude of single nucleotide polymorphisms (SNPs) are listed in public SNP databases.

The inventors investigated 95 SNPs, 74 of which were polymorphic (average intermarker distance: 3.5 kb) and thus included in the statistical evaluation. The genetic variability of all polymorphic SNPs and the recovery from depressive symptoms were examined in a summarizing model using Fisher's product method. After correction for multiple testing a highly significant association was found between the genotypes or allele frequencies of the ABCB1 gene and the remission in weeks 4, 5 and 6 only in patients receiving substrates of P-gp (Table 3). For a better presentation of the clinical course and involvement of the entire period up to week 6 including all patients enrolled in the study a Cox regression survival analysis was performed. As demonstrated in FIG. 3 and Table 4, only the patients receiving substrates of P-gp showed genotype-dependent, highly significant target parameter differences during the clinical course, achieving a remission with a score of <10 on the HAM-D (FIG. 3, Table 4).

Mainly responsible for this association were the SNPs rs2235067, rs4148740, rs10280101, rs7787082, rs2032583, rs4148739, rs11983225, rs10248420, rs2235040, rs12720067 and rs2235015, showing p-values of <0.001 in the ANOVA analysis (Table 3). In an attempt to narrow down the region of ABCB1 possibly causing differential response, the linkage disequilibrium (LD) structure of ABCB1 was analyzed using HAPLOVIEW. With the exception of rs2235015 all highly associated SNPs were located in a single haplotype block (FIG. 4), and the SNPs rs2235067, rs4148740, rs2032583, rs4148739, rs11983225, s2235040, rs12720067 as well as the SNPs rs7787082 and rs10248420 exhibited an r-square of >0.8 with each other. All highly associated SNPs are located in introns and with a D' of more than 90% in linkage disequilibrium (LD) with the best examined exon SNPs rs1045642 (C3435T), rs2032582 (G2677T) and rs1128503 (C1236T). In both the synonymous SNPs rs2032582 (exon 21) and rs1128503 (exon 12) and the non-synonymous SNP rs1045642 (exon 26) the known genetic variabilities result in different P-gp functions (Kimchi-Sarfaty et al., 2007). However, the r-square values are comparatively low (in the range of 15%) and there is no significant association between these SNPs in the exons and the remission.

As exemplified in FIG. 2 for the SNP rs2232583 the genotype distribution differs between the patient group with remission versus the group without remission among patients treated for 4 weeks with a P-gp substrate (Cochran-Armitage test, p=0.00007). The probability of being remitted from depression after 4 weeks is increased for C-carriers treated with substrates of P-gp (odds ratio: 7.72, p=0.000065). In contrast, it was predictable that patients carrying the TT genotype will not be remitted after a 4-week treatment period. In the group of patients receiving the non-substrate mirtazapine there was no difference found between the genotypes of remitters and non-remitters. The group characteristics for the representative SNP rs2032583, depending on the genotype, did not differ between the two subgroups "patients treated with P-gp substrates" and "patients treated with non-P-gp substrates" (Table 6).

The Cox regression analysis did not reveal any significant differences for remission (HAM-R<10) in the first 6 weeks (Wald value=0.125; sig=0.72) between the subgroup of patients receiving drugs that are substrates of P-pg and the subgroup of patients receiving drugs that are not substrates of P-gp, allowing to reject the possibility that differences in drug efficacy accounts for our different findings. In fact, the drugs used here proved to be especially effective according to large comparative studies required for approval. It is only the combined consideration of both the patient's ABCB1 genotype and the medication's P-gp substrate status that identifies a group of patients who exhibit a clearly better remission rate than patient populations assembled on the basis of the patient's genotype or the medication's P-gp substrate status alone.

SNPs in ABCB1 have been reported to influence intestinal uptake and thus plasma levels of drugs (Hoffmeyer et al., 2000; Brinkmann, 2002; Sakaeda et al., 2003). However, the various genotype-dependant remission rates found in this study were not due to different doses or plasma drug levels, which underscores that monitoring plasma antidepressant levels is not reliable to predict adequacy of treatment.

Recently, McMahon et al. (2006) reported that African-Americans responded less well to an established antidepressant than Caucasians. They accounted this difference to the global higher frequency of the A-allele in a specific SNP in the serotonin 2 A receptor gene. In this context it is noteworthy that also in the ABCB1 gene and particularly in the SNPs it was reported that in the prediction of treatment outcome considerable ethnic variability occurs (Kim, 2002; Tang et al., 2002, 2004; Kroetz et al., 2003). Thus, the current finding indicates that variant ABCB1 genotypes contribute to differences in treatment outcome across ethnic groups and further encourage studies to elucidate the clinical implications of these differences across ethnic groups.

The general conclusion to be drawn is that any drug administered to treat CNS diseases should be analyzed for its P-gp substrate status, which can be determined by using abcb1ab knockout mice. From a clinical point of view, the findings warrant that patients receiving a drug that is a P-gp substrate for the treatment of brain diseases are genotyped to exclude the possibility that a patient receives a drug that fails to enter the CNS to an extent required for efficacy. The combination of therapeutic drug monitoring (TDM) involving enteral drug intake and cytochrome P450 drug metabolism and P-gp genotyping for detecting the drug's bioavailability in the brain may predict the response of an individual patient to a certain drug. Finally, the interdependence of P-gp substrate capacity and ABCB1 genotype needs to be considered in future CNS development, because drugs that differ in their P-gp substrate capacity need to be evaluated in clinical trials where study populations are stratified according to the ABCB1 genotype.

TABLES

TABLE 1

Inhibitors and Modulators of ABCB1

| Substance | Substrate | Inhibitor | Inducer |
|---|---|---|---|
| Antiacids | | | |
| Cimetidine | x | | |
| Lansoprazole | x | x | |
| Omeprazol | | x | |
| Pantoprazole | | x | |
| Ranitidine | x | | |
| Antiarrhythmics | | | |
| Amiloride | x | x | |
| Amiodarone | | x | |
| Barnidipine | | x | |
| Benidipine | | x | |
| Bepridil | | x | |
| Digitoxin | x | | |
| Digoxin | x | | |
| Efonidipine | | x | |
| Manidipine | | | |
| Niguldipine | | x | |
| Nilvadipine | | x | |
| Propafenone | | x | |
| Propranolol | | x | |
| Quinidine | x | x | |
| Verapamil | x | x | |
| Antibiotics | | | |
| Amoxicillin | x | | |
| Ceftriaxone | | x | |
| Ciprofloxacin | x | | |
| Clarithromycin | | x | |
| Enoxacin | x | | |
| Erythromycin | x | x | |

TABLE 1-continued

Inhibitors and Modulators of ABCB1

| Substance | Substrate | Inhibitor | Inducer |
|---|---|---|---|
| Fucidine | | x | |
| Josamycin | | x | |
| Levofloxacin | x | | |
| Ofloxacin | (x) | x | |
| Rifampin | x | | x |
| Sparfloxacin | x | | |
| Tetracycline | x | | |
| Anticancer agents | | | |
| Actinomycin D | x | | |
| Adriamycin | x | | |
| Azidopine | x | x | |
| Daunorubicin | x | | |
| Docetaxel | x | | |
| Doxorubicin | x | | x |
| Epirubicin | x | | |
| Etoposide | x | | |
| Gramicidine | | x | |
| Imatinib | x | | |
| Irinotecan | x | | |
| Mitomycin C | x | (x) | |
| Mitoxantrone | x | | |
| Paclitaxel | x | x | |
| Quercetin | | x | |
| Teniposide | x | | |
| Topotecan | x | | |
| Valinomycin | | x | |
| Vinblastine | x | | |
| Vincristine | x | | |
| Vindesine | x | | |
| Vinorelbine | x | | |
| Antidepressants | | | |
| Amitriptyline | x | | |
| Citalopram | x | x | |
| Desipramine | | x | |
| Doxepine | x | | |
| Flesinoxan | x | | |
| Fluoxetine | | x | |
| Fluvoxamine | | x | |
| Imipramine | | x | |
| Maprotiline | | x | |
| Nefazodone | | x | (x) |
| Nortriptyline | x | | |
| Paroxetine | | x | |
| Reboxetine | | x | |
| Sertraline | | x | |
| St John's wort | | | x |
| Trazodone | | | (x) |
| Trimipramine | x | x | |
| Venlafaxine | x | x | |
| Antiemetics | | | |
| Domperidone | x | | |
| Ondansetron | x | | |
| Antiepileptics | | | |
| Carbamazepine | x | | |
| Felbamate | x | | |
| Lamotrigin | x | | |
| Phenobarbital | x | | |
| Phenytoin | x | | |
| Antihypertensive agents | | | |
| Carvedilol | | x | |
| Celiprolol | x | | |
| Diltiazem | x | | |
| Doxazosin | | x | |
| Felodipine | | x | |
| Losartan | x | | |
| Mibefradil | x | x | |
| Nifedipine | | x | |
| Nicardipine | | x | |
| Nitrendipine | | x | |
| Prazosin | | | x |

TABLE 1-continued

Inhibitors and Modulators of ABCB1

| Substance | Substrate | Inhibitor | Inducer |
|---|---|---|---|
| Reserpine |  | x |  |
| Talinolol | x |  |  |
| Antimycotics |  |  |  |
| Fluconazole |  |  |  |
| Itraconazole | x | x |  |
| Ketoconazole |  | x |  |
| Antiparkinson |  |  |  |
| Amantadine |  |  |  |
| Budipin | x |  |  |
| L-Dopa | x |  |  |
| Antiviral agents |  |  |  |
| Amprenavir | x |  | x |
| Indinavir | x | x | x |
| Lopinavir |  | x | x |
| Nelfinavir | x | x | x |
| Ritonavir | x | x | x |
| Saquinavir | x | x | x |
| Glucocorticoids |  |  |  |
| Aldosterone | x |  |  |
| Cortisol | x |  |  |
| Dexamethasone | x |  | x |
| Hydrocortisone | x |  |  |
| Methylprednisolone | x |  |  |
| Immunosuppressants |  |  |  |
| Cyclosporine | x | x |  |
| FK 506 |  | x |  |
| Methotrexat |  |  |  |
| Rapamycin | x | x |  |
| Sirolimus | x | x |  |
| Tacrolimus | x | x |  |
| Tamoxifen |  | x |  |
| Valspodar (PSC833) | x | x |  |
| Vinblastine |  | x |  |
| Statins |  |  |  |
| Atorvastatin | x | x |  |
| Lovastatin |  | x |  |
| Simvastatin |  | x |  |
| Neuroleptics |  |  |  |
| Chloropromazine |  | x |  |
| Clozapine |  |  |  |
| Droperidol |  | x |  |
| Flupenthixol |  | x |  |
| Fluphenazine |  | x |  |
| Haloperidol |  | (x) |  |
| Melperon |  |  |  |
| Olanzapine | (x) |  |  |
| Phenothiazine |  | x | x |
| Pimozide |  | x |  |
| Prochlorpemazine |  | x |  |
| Promethazine |  | x |  |
| Quetiapine | x |  |  |
| Risperidone | x |  |  |
| Sulpiride | x |  |  |
| Thioridazine |  | x |  |
| Trifluoperazine |  | x |  |
| Triflupromazine |  | x |  |
| Opioids |  |  |  |
| Alfentanil |  | x |  |
| Fentanyl | x | x |  |
| Methadone |  | x |  |
| Morphine | x |  | x |
| Pentazocine |  | x |  |
| Sufentanil |  | x |  |
| Surfactants |  |  |  |
| Cremophor EL |  | x |  |
| Triton X-100 |  | x |  |
| Tween 80 |  | x |  |
| Others |  |  |  |
| Albendazole |  |  |  |
| Anti-CD19 antibody |  | x |  |
| Azelastine |  | x |  |
| Bilirubin | x |  |  |
| Bisantrene |  | x |  |
| Bromocriptine |  | x |  |
| Bunitrolol | x |  |  |
| Celiprolol | x |  |  |
| Chloroquine |  | (x) |  |
| Chlorpheniramine |  |  |  |
| Cholesterol | x | x |  |
| Colchicine | x |  |  |
| Cortexolone |  |  |  |
| Cyproheptadin |  | x |  |
| Debrisoquine | x |  |  |
| Dihydrotestosterone | x |  |  |
| Dipyridamole |  | x |  |
| DM27 |  |  |  |
| DM40 |  |  |  |
| E6 |  | x |  |
| Emetine |  | x |  |
| EP 51389 |  | x |  |
| Estradiol | x |  |  |
| Fexofenadine | x |  |  |
| Flavinoids |  | x |  |
| Flunitrazepam |  |  |  |
| Garlic |  | x |  |
| GF120918 |  | x |  |
| Ginsenoide |  | x |  |
| Grapefruit |  | x | (x) |
| Green Tea |  | x | x |
| H2O2 |  |  | x |
| Ivermectin | x |  |  |
| Lidocaine |  | x |  |
| Lonafarnib (SCH66336) |  | x |  |
| Loperamide | x |  |  |
| Loratadine | (x) | (x) |  |
| Mefloquine | x | x |  |
| Midazolam | x | (x) |  |
| Nobilitin |  | x |  |
| orange juice-Seville |  | x |  |
| Pipeline |  | x |  |
| Probenecid |  | x |  |
| Progesterone |  | x |  |
| Quinacrine |  | x |  |
| Quinine |  | x |  |
| Retinoic acid |  |  | x |
| Rhodamine 123 | x |  |  |
| RU 486 |  | x |  |
| Spironolactone |  | x |  |
| Sumatriptan |  |  |  |
| Terfenadine | x | x |  |
| 1,2,3,4-tetrahydroisoquinoline |  | x |  |
| Tetrandrine |  | x |  |
| Thyroid Hormones | x | x |  |
| TNF alpha |  | x |  |
| Unconjugated Bilirubin | x |  | x |
| Vandate |  | x |  |
| Vecuronium | x |  |  |
| Vitamin A |  |  | x |
| XR9576 |  | x |  |
| Yohimbin |  | x |  |
| Zosuquidar•3HCl |  | x |  |
| Elacridar (GF120918) |  | x |  |
| LY335979 |  | x |  |
| Tariquidar (XR9576) |  | x |  |

TABLE 2

Organ concentrations of antidepressant drugs and their metabolites after 11 days of subcutaneous administration via osmotic pumps.

Citalopram [ng/g or ml]

| | abcb1ab (−/−) | SEM | control | SEM | ratio (−/−)/(+/+) | Significance |
|---|---|---|---|---|---|---|
| plasma | 89.37 | 8.65 | 106.71 | 7.60 | 0.8 | ns |
| cerebrum | 480.93 | 27.39 | 158.27 | 15.84 | 3.0 | * |
| spleen | 468.29 | 42.16 | 446.96 | 46.93 | 1.0 | ns |
| kidney | 795.74 | 50.39 | 962.29 | 87.92 | 0.8 | ns |
| liver | 240.33 | 16.40 | 238.02 | 18.46 | 1.0 | ns |
| lung | 1238.47 | 124.86 | 1238.71 | 105.37 | 1.0 | ns |
| testes | 687.92 | 28.30 | 428.19 | 35.05 | 1.6 | * |

Group effect: $F(7, 8) = 35.4$; significance of $F < 0.001$

Venlafaxine [ng/g or ml]

| | abcb1ab (−/−) | SEM | control | SEM | ratio (−/−)/(+/+) | Significance |
|---|---|---|---|---|---|---|
| plasma | 70.57 | 4.22 | 71.37 | 3.34 | 1.0 | ns |
| cerebrum | 456.32 | 19.76 | 261.14 | 9.54 | 1.7 | * |
| spleen | 564.20 | 23.00 | 581.95 | 11.31 | 1.0 | ns |
| kidney | 1054.88 | 37.58 | 1035.27 | 23.67 | 1.0 | ns |
| liver | 323.22 | 17.09 | 314.59 | 22.03 | 1.0 | ns |
| lung | 672.59 | 36.14 | 747.38 | 36.16 | 0.9 | ns |
| testes | 842.61 | 9.88 | 715.92 | 21.29 | 1.2 | * |

Group effect: $F(7, 8) = 30.7$; significance of $F < 0.001$

D-Venlafaxine [ng/g or ml]

| | abcb1ab (−/−) | SEM | control | SEM | ratio (−/−)/(+/+) | Significance |
|---|---|---|---|---|---|---|
| plasma | 5.98 | 0.70 | 5.50 | 1.12 | 1.1 | ns |
| cerebrum | 36.99 | 4.86 | 8.97 | 2.57 | 4.1 | * |
| spleen | 33.80 | 3.42 | 29.42 | 3.76 | 1.1 | ns |
| kidney | 127.32 | 22.51 | 107.88 | 12.72 | 1.2 | ns |
| liver | 88.22 | 10.60 | 83.15 | 8.15 | 1.1 | ns |
| lung | 44.91 | 3.85 | 50.63 | 7.09 | 0.9 | ns |
| testes | 39.19 | 2.64 | 30.18 | 4.01 | 1.3 | ns |

Group effect: $F(7, 8) = 4.8$; significance of $F = 0.022$

Mirtazapine [ng/g or ml]

| | abcb1ab (−/−) | SEM | control | SEM | ratio (−/−)/(+/+) | significance |
|---|---|---|---|---|---|---|
| plasma | 11.17 | 1.19 | 7.66 | 1.59 | 1.5 | ns |
| cerebrum | 51.31 | 4.84 | 34.90 | 6.20 | 1.5 | ns |
| spleen | 86.19 | 10.75 | 67.54 | 14.27 | 1.3 | ns |
| kidney | 91.22 | 9.75 | 70.93 | 13.29 | 1.3 | ns |
| liver | 20.59 | 2.14 | 12.39 | 2.43 | 1.7 | ns |
| lung | 105.36 | 9.64 | 61.47 | 11.75 | 1.7 | ns |
| testes | 110.29 | 12.14 | 61.22 | 11.59 | 1.8 | ns |
| intestine | 24.58 | 2.61 | 19.96 | 3.33 | 1.2 | ns |

Group effect: $F(8, 9) = 3.0$; significance of $F = 0.58$
* = significant difference; ns = not significant

TABLE 3

ANOVA analysis of the association between remission and SNPs Empiric p-values of the ANOVA analysis determined by applying $10^6$ permutations and corrected for age and sex for both the entire group (all patients) and the two subgroups of patients receiving amitriptyline, citalopram, paroxetine or venlafaxine (substrates of P-gp) or mirtazapine (non-P-gp-substrate).

| | All patients Remission (HDRS < 10) | | | | Substrates of P-gp Remission (HDRS < 10) | | | | Non-substrates of P-gp Remission (HDRS < 10) | | | |
|---|---|---|---|---|---|---|---|---|---|---|---|---|
| dbSNP ID | N | Week 4 | Week 5 | Week 6 | N | Week 4 | Week 5 | Week 6 | N | Week 4 | Week 5 | Week 6 |
| rs4148809 | 267 | 0.199 | 0.466 | 0.313 | 93 | 0.477 | 0.344 | 0.803 | 70 | 0.582 | 0.156 | 0.574 |
| rs2888611 | 268 | 0.980 | 0.907 | 0.826 | 94 | 0.671 | 0.114 | 0.179 | 70 | 0.777 | 0.925 | 0.658 |
| rs6979325 | 268 | 0.282 | 0.134 | 0.355 | 94 | 0.020 | 0.045 | 0.037 | 70 | 1.000 | 1.000 | 1.000 |
| rs2178658 | 268 | 0.760 | 0.687 | 0.870 | 94 | 0.754 | 0.856 | 0.938 | 70 | 0.498 | 0.091 | 0.662 |
| rs7789645 | 269 | 0.919 | 0.864 | 0.755 | 94 | 0.779 | 0.156 | 0.242 | 70 | 0.777 | 0.926 | 0.658 |
| rs7793196 | 268 | 0.929 | 0.872 | 0.827 | 94 | 0.779 | 0.156 | 0.242 | 70 | 0.779 | 0.924 | 0.944 |
| rs1055302 | 270 | 0.181 | 0.374 | 0.400 | 96 | 0.531 | 0.513 | 0.529 | 70 | 0.658 | 0.445 | 0.568 |
| rs17064 | 215 | 0.362 | 0.901 | 0.377 | 79 | 0.132 | 0.516 | 0.227 | 59 | 0.837 | 0.310 | 0.423 |
| rs2235048 | 353 | 0.427 | 0.010 | 0.482 | 112 | 0.280 | 0.108 | 0.164 | 85 | 0.861 | 0.477 | 0.331 |
| rs1045642 | 351 | 0.316 | 0.044 | 0.483 | 112 | 0.240 | 0.204 | 0.119 | 85 | 0.860 | 0.473 | 0.268 |
| rs6949448 | 268 | 0.593 | 0.046 | 0.594 | 94 | 0.239 | 0.188 | 0.224 | 70 | 0.196 | 0.048 | 0.728 |
| rs7779562 | 344 | 0.423 | 0.406 | 0.277 | 110 | 0.434 | 0.866 | 0.482 | 84 | 0.325 | 1.000 | 1.000 |
| rs2235067 | 272 | 0.047 | 0.0085 | 0.978 | 97 | 0.000075 | 0.0033 | 0.030 | 70 | 0.902 | 0.0024 | 0.927 |
| rs4148744 | 229 | 0.465 | 0.577 | 0.967 | 84 | 0.368 | 0.879 | 0.485 | 62 | 0.475 | 1.000 | 1.000 |
| rs4148743 | 228 | 0.351 | 0.046 | 0.500 | 84 | 0.387 | 0.437 | 0.174 | 61 | 0.770 | 0.362 | 0.510 |
| rs4148740 | 267 | 0.123 | 0.030 | 0.756 | 93 | 0.000031 | 0.0048 | 0.011 | 70 | 0.442 | 0.017 | 0.759 |
| rs10280101 | 264 | 0.217 | 0.052 | 0.770 | 92 | 0.000056 | 0.013 | 0.0053 | 69 | 0.444 | 0.018 | 0.732 |
| rs7787082 | 265 | 0.035 | 0.011 | 0.497 | 91 | 0.000048 | 0.00011 | 0.0052 | 70 | 0.526 | 0.069 | 0.807 |
| rs2032583 | 355 | 0.049 | 0.0038 | 0.221 | 114 | 0.000034 | 0.0035 | 0.016 | 86 | 0.658 | 0.003 | 0.931 |
| rs2032582 | 268 | 0.294 | 0.171 | 0.956 | 94 | 0.251 | 0.450 | 0.276 | 68 | 0.538 | 0.197 | 0.837 |
| rs4148739 | 268 | 0.118 | 0.028 | 0.756 | 93 | 0.000031 | 0.0048 | 0.011 | 71 | 0.460 | 0.016 | 0.759 |
| rs11983225 | 265 | 0.111 | 0.031 | 0.742 | 91 | 0.000036 | 0.0061 | 0.012 | 70 | 0.442 | 0.017 | 0.844 |
| rs4148738 | 344 | 0.287 | 0.023 | 0.890 | 110 | 0.212 | 0.059 | 0.125 | 84 | 0.095 | 0.109 | 0.771 |
| rs10248420 | 264 | 0.039 | 0.010 | 0.566 | 91 | 0.00010 | 0.00021 | 0.010 | 69 | 0.596 | 0.046 | 0.807 |
| rs2235040 | 266 | 0.019 | 0.038 | 0.846 | 93 | 0.0000070 | 0.0016 | 0.012 | 67 | 0.983 | 0.012 | 0.934 |
| rs12720067 | 211 | 0.124 | 0.029 | 0.719 | 92 | 0.000021 | 0.0059 | 0.0023 | 71 | 0.460 | 0.016 | 0.759 |
| rs1922242 | 228 | 0.487 | 0.844 | 0.821 | 82 | 0.252 | 0.725 | 0.859 | 61 | 0.052 | 0.741 | 0.708 |
| rs2235046 | 355 | 0.132 | 0.041 | 0.941 | 113 | 0.137 | 0.063 | 0.072 | 86 | 0.177 | 0.124 | 0.816 |
| rs2235013 | 268 | 0.381 | 0.023 | 0.400 | 93 | 0.057 | 0.147 | 0.280 | 71 | 0.566 | 0.056 | 0.324 |

TABLE 3-continued

ANOVA analysis of the association between remission and SNPs Empiric p-values of the ANOVA analysis determined by applying $10^6$ permutations and corrected for age and sex for both the entire group (all patients) and the two subgroups of patients receiving amitriptyline, citalopram, paroxetine or venlafaxine (substrates of P-gp) or mirtazapine (non-P-gp-substrate).

| dbSNP ID | All patients Remission (HDRS < 10) | | | | Substrates of P-gp Remission (HDRS < 10) | | | | Non-substrates of P-gp Remission (HDRS < 10) | | | |
|---|---|---|---|---|---|---|---|---|---|---|---|---|
| | N | Week 4 | Week 5 | Week 6 | N | Week 4 | Week 5 | Week 6 | N | Week 4 | Week 5 | Week 6 |
| rs2235035 | 249 | 0.877 | 0.672 | 0.252 | 87 | 0.564 | 0.602 | 0.399 | 64 | 0.446 | 0.433 | 0.355 |
| rs2235033 | 344 | 0.135 | 0.043 | 0.830 | 110 | 0.087 | 0.104 | 0.312 | 84 | 0.209 | 0.042 | 0.374 |
| rs2032588 | 227 | 0.562 | 0.654 | 0.046 | 82 | 0.352 | 0.854 | 0.356 | 60 | 0.351 | 0.290 | 0.135 |
| rs1128503 | 270 | 0.252 | 0.033 | 0.446 | 94 | 0.144 | 0.129 | 0.140 | 71 | 0.263 | 0.045 | 0.605 |
| rs2229109 | 262 | 0.545 | 0.277 | 0.084 | 93 | 0.560 | 0.468 | 1.000 | 63 | | | |
| rs10276036 | 269 | 0.246 | 0.031 | 0.426 | 94 | 0.144 | 0.129 | 0.140 | 71 | 0.263 | 0.045 | 0.605 |
| rs1922240 | 269 | 0.939 | 0.203 | 0.163 | 94 | 0.645 | 0.262 | 0.323 | 71 | 0.259 | 0.856 | 0.190 |
| rs2235023 | 269 | 0.399 | 0.798 | 0.470 | 94 | 0.763 | 0.452 | 0.273 | 68 | 0.818 | 0.768 | 0.503 |
| rs1202169 | 355 | 0.170 | 0.062 | 0.816 | 113 | 0.185 | 0.090 | 0.109 | 86 | 0.411 | 0.088 | 0.692 |
| rs1202168 | 270 | 0.383 | 0.100 | 0.799 | 94 | 0.200 | 0.163 | 0.177 | 68 | 0.565 | 0.170 | 0.831 |
| rs1202167 | 227 | 0.557 | 0.030 | 0.502 | 83 | 0.264 | 0.191 | 0.179 | 62 | 0.860 | 0.278 | 0.882 |
| rs2235019 | 228 | 0.496 | 0.406 | 0.067 | 84 | | | | 62 | | | |
| rs2235017 | 229 | 0.685 | 0.596 | 0.448 | 84 | | | | 62 | | | |
| rs2235015 | 350 | 0.155 | 0.0043 | 0.029 | 113 | 0.0015 | 0.0013 | 0.00026 | 85 | 0.810 | 0.051 | 0.520 |
| rs6950978 | 267 | 0.728 | 0.902 | 0.141 | 93 | 0.354 | 0.956 | 0.492 | 70 | 0.566 | 0.499 | 0.417 |
| rs10256836 | 268 | 0.815 | 0.892 | 0.126 | 94 | 0.475 | 0.942 | 0.460 | 70 | 0.556 | 0.540 | 0.359 |
| rs10264990 | 265 | 0.758 | 0.881 | 0.112 | 91 | 0.676 | 0.646 | 0.224 | 70 | 0.685 | 0.341 | 0.988 |
| rs1202179 | 272 | 0.393 | 0.085 | 0.250 | 97 | 0.115 | 0.214 | 0.039 | 70 | 0.362 | 0.030 | 0.083 |
| rs1989831 | 228 | 0.413 | 0.049 | 0.057 | 83 | 0.096 | 0.249 | 0.028 | 62 | 0.507 | 0.062 | 0.160 |
| rs1202172 | 355 | 0.555 | 0.127 | 0.285 | 114 | 0.074 | 0.033 | 0.0071 | 86 | 0.192 | 0.040 | 0.083 |
| rs1202171 | 271 | 0.412 | 0.092 | 0.266 | 96 | 0.125 | 0.240 | 0.046 | 70 | 0.362 | 0.029 | 0.083 |
| rs17327442 | 267 | 0.921 | 0.442 | 0.227 | 93 | 0.805 | 0.449 | 0.451 | 70 | 0.414 | 0.727 | 0.201 |
| rs4148733 | 227 | 0.786 | 0.468 | 0.103 | 82 | 0.610 | 0.376 | 0.548 | 62 | 0.396 | 0.724 | 0.223 |
| rs1202186 | 225 | 0.420 | 0.061 | 0.076 | 82 | 0.209 | 0.152 | 0.014 | 62 | 0.507 | 0.062 | 0.160 |
| rs1202185 | 228 | 0.413 | 0.049 | 0.057 | 83 | 0.096 | 0.249 | 0.028 | 62 | 0.507 | 0.062 | 0.160 |
| rs1202182 | 228 | 0.413 | 0.050 | 0.057 | 83 | 0.096 | 0.249 | 0.028 | 62 | 0.499 | 0.061 | 0.158 |
| rs1202181 | 200 | 0.722 | 0.031 | 0.080 | 77 | 0.087 | 0.085 | 0.0049 | 51 | 0.358 | 0.045 | 0.686 |
| rs2188525 | 269 | 0.854 | 0.955 | 0.509 | 94 | 0.903 | 0.405 | 0.584 | 71 | 1.000 | 1.000 | 1.000 |
| rs2235074 | 226 | 0.551 | 0.553 | 0.991 | 81 | 0.337 | 0.677 | 0.524 | 60 | 1.000 | 1.000 | 1.000 |
| rs2214102 | 202 | 0.226 | 0.237 | 0.247 | 75 | 0.151 | 0.263 | 0.261 | 54 | 0.447 | 0.366 | 1.000 |
| rs4728709 | 237 | 0.261 | 0.742 | 0.661 | 91 | 0.475 | 0.637 | 0.862 | 70 | 0.777 | 0.343 | 0.462 |
| rs4148731 | 227 | 0.136 | 0.560 | 0.782 | 83 | | | | 61 | | | |
| rs4148730 | 226 | 0.132 | 0.698 | 0.700 | 80 | | | | 62 | | | |
| rs13233308 | 267 | 0.146 | 0.968 | 0.453 | 93 | 0.308 | 0.604 | 0.585 | 70 | 0.256 | 0.173 | 0.138 |
| rs4148729 | 229 | 0.133 | 0.560 | 0.782 | 84 | | | | 62 | | | |
| rs10264856 | 339 | 0.097 | 0.595 | 0.672 | 110 | 0.265 | 0.380 | 0.853 | 83 | 0.754 | 1.000 | 1.000 |
| rs2157926 | 228 | 0.369 | 0.633 | 0.772 | 81 | 0.171 | 0.535 | 0.836 | 63 | 0.782 | 1.000 | 1.000 |
| rs10245878 | 269 | 0.761 | 0.237 | 0.583 | 94 | 0.520 | 0.975 | 0.869 | 71 | 0.744 | 0.019 | 0.047 |
| rs10267099 | 344 | 0.813 | 0.483 | 0.922 | 110 | 0.365 | 0.647 | 0.791 | 84 | 0.634 | 0.109 | 0.314 |
| rs7796247 | 344 | 0.068 | 0.487 | 0.954 | 110 | | | | 84 | | | |
| rs2188529 | 221 | 0.160 | 0.794 | 0.548 | 81 | | | | 59 | | | |
| rs4148727 | 220 | 0.133 | 0.560 | 0.782 | 80 | | | | 62 | | | |
| rs10275625 | 333 | 0.068 | 0.487 | 0.954 | 110 | | | | 84 | | | |

TABLE 4

Fisher's product and Westfall/Young analysis
An analysis of all polymorphic SNPs and phenotypes was conducted according to Fisher's product method (FPM) for the genotypic und allelic models. For FPM, as a single statistic is formed, no further correction for multiple testing is necessary. We also give result for the minimum P of Westfall and Young, which is a more conventional method controlling the family-wise error rate.

| Remission | | All patients | | Substrates of P-gp | | Non-substrates of P-gp | |
|---|---|---|---|---|---|---|---|
| | | Fisher's product | Westfall/ Young | Fisher's product | Westfall/ Young | Fisher's product | Westfall/ Young |
| Fisher's product and Westfall/Young correction over all SNPs | | | | | | | |
| 4 weeks | Genotypic | 0.191 | 0.466 | 0.00034 | 0.00011 | 0.775 | 0.712 |
| 4 weeks | Allelic | 0.136 | 0.678 | 0.00039 | 0.000048 | 0.565 | 0.829 |
| 5 weeks | Genotypic | 0.015 | 0.132 | 0.0084 | 0.0042 | 0.014 | 0.056 |
| 5 weeks | Allelic | 0.005 | 0.039 | 0.0019 | 0.0021 | 0.160 | 0.137 |

TABLE 4-continued

Fisher's product and Westfall/Young analysis
An analysis of all polymorphic SNPs and phenotypes was conducted according to Fisher's product method (FPM) for the genotypic und allelic models. For FPM, as a single statistic is formed, no further correction for multiple testing is necessary. We also give result for the minimum P of Westfall and Young, which is a more conventional method controlling the family-wise error rate.

| Remission | | All patients | | Substrates of P-gp | | Non-substrates of P-gp | |
|---|---|---|---|---|---|---|---|
| | | Fisher's product | Westfall/Young | Fisher's product | Westfall/Young | Fisher's product | Westfall/Young |
| 6 weeks | Genotypic | 0.513 | 0.615 | 0.0071 | 0.013 | 0.644 | 0.621 |
| 6 weeks | Allelic | 0.327 | 0.233 | 0.0012 | 0.00049 | 0.904 | 0.856 |
| Fisher's product and Westfall/Young correction over all SNPs and over all Phenotypes | | | | | | | |
| | Genotypic | 0.068 | 0.309 | 0.00036 | 0.00040 | 0.160 | 0.136 |
| | Allelic | 0.024 | 0.099 | 0.000094 | 0.00016 | 0.557 | 0.340 |

TABLE 5

Cox regression analysis of genotype-dependant remission
For all SNPs showing a highly significant association between genotype and remission in the FPM a Cox regression was performed and the Wald values and p-values shown. testing carriers of the rarer allele versus non-carriers.

| | All patients | | Substrates of P-gp | | Non-substrates of P-gP | |
|---|---|---|---|---|---|---|
| SNP | Wald | p-value | Wald | p-value | Wald | p-value |
| rs2235067 | 1.902 | 0.168 | 10.586 | 0.0011 | 0.214 | 0.644 |
| rs4148740 | 1.938 | 0.164 | 14.424 | 0.00015 | 0.157 | 0.692 |
| rs10280101 | 1.493 | 0.222 | 13.119 | 0.00029 | 0.115 | 0.734 |
| rs7787082 | 3.126 | 0.077 | 9.115 | 0.0025 | 0.454 | 0.500 |
| rs2032583 | 3.218 | 0.073 | 13.277 | 0.00027 | 0.758 | 0.384 |
| rs4148739 | 1.991 | 0.158 | 14.424 | 0.00015 | 0.175 | 0.675 |
| rs11983225 | 2.486 | 0.115 | 13.636 | 0.00022 | 0.440 | 0.507 |
| rs10248420 | 3.374 | 0.066 | 9.115 | 0.0025 | 0.566 | 0.452 |
| rs2235040 | 2.285 | 0.131 | 10.109 | 0.0015 | 0.353 | 0.552 |
| rs12720067 | 2.624 | 0.105 | 15.289 | 0.000092 | 0.175 | 0.675 |
| rs2235015 | 2.970 | 0.085 | 9.197 | 0.0024 | 0.008 | 0.931 |

TABLE 6

Genotype-dependent group characteristics for rs2032583
The group characteristics number of patients (% women), age, HDRS at inclusion, age at onset, illness duration in years, previous episodes, number of previous hospitalizations, duration of actual episode, ethnicity, co-medication and diagnosis are shown for each genotype. It was investigated in an ANOVA analysis whether there are significant differences between the CC, CT and TT groups (Sig). The Table shows the results of all patients, patients receiving substrates of P-gps and patients receiving non-P-gp-substrates.

| | CC | CT | TT | Sig. |
|---|---|---|---|---|
| All patients | | | | |
| N (% women) | 7 (57.1%) | 84 (55.9%) | 344 (57.2%) | 0.97 |
| Age | 48 ± 4.3 | 48.6 ± 1.4 | 48.3 ± 0.8 | 0.98 |
| HAM-D at inclusion | 30.7 ± 2.8 | 26.5 ± 0.7 | 26.4 ± 0.3 | 0.22 |
| Age at onset | 40.8 ± 6.8 | 38 ± 1.6 | 36 ± 0.8 | 0.44 |
| Illness duration (years) | 7.1 ± 3.3 | 10.7 ± 1.2 | 12.3 ± 0.7 | 0.36 |
| Previous episodes | 1.1 ± 0.5 | 3 ± 0.6 | 2.6 ± 0.2 | 0.58 |
| Previous hospitalization | 0.7 ± 0.4 | 1.2 ± 0.2 | 1.7 ± 0.3 | 0.71 |
| Duration of actual | 41.5 ± 8.5 | 38.4 ± 7.3 | 38.1 ± 3.7 | 0.99 |
| Caucasian | 100% | 100% | 100% | |
| German origin | 100% | 83.5% | 85.5% | 0.87 |
| Neuroleptics | 57.1% | 10.7% | 18% | 0.01 |
| Mood stabilizers | 14.2% | 16.6% | 17.4% | 1.00 |
| Lithium | 0% | 9.5% | 6.7% | 0.62 |
| Benzodiazepines | 14.2% | 28.5% | 31.1% | 0.67 |
| Single episode | 42.8% | 28.5% | 31.9% | 0.61 |
| Recurrent depression | 57.1% | 57.1% | 52.7% | 0.77 |
| Bipolar II | 0% | 13% | 12.3% | 0.88 |
| Dysthymia | 0% | 1.1% | 0.5% | 0.51 |
| Schizoaffective disorder | 0% | 0% | 1.4% | 0.62 |
| Adjustment disorder | 0% | 0% | 0.8% | 1.00 |
| Substrates of P-gp | | | | |
| N (% women) | 2 (50%) | 21 (61.9%) | 110 (59%) | 1.00 |
| Age | 44.5 ± 9.5 | 48.2 ± 3 | 45 ± 1.4 | 0.66 |
| HAM-D at inclusion | 29 ± 1 | 25.1 ± 1.5 | 26.7 ± 0.6 | 0.57 |
| Age at onset | 43.5 ± 9.5 | 36.9 ± 3.2 | 33.3 ± 1.4 | 0.43 |
| Illness duration (years) | 1 ± 0 | 12.1 ± 2.2 | 11.6 ± 1.1 | 0.41 |
| Previous episodes | 0.5 ± 0.5 | 1.6 ± 0.5 | 2.7 ± 0.5 | 0.64 |
| Previous hospitalization | 0.5 ± 0.5 | 1.2 ± 0.4 | 1.1 ± 0.1 | 0.82 |
| Duration of actual | 20 ± 4 | 32.2 ± 8.2 | 38 ± 6.3 | 0.86 |
| Caucasian | 100% | 100% | 100% | |
| German origin | 100% | 89.4% | 84.6% | 0.80 |
| Neuroleptics | 0% | 19% | 16.3% | 0.83 |
| Mood stabilizers | 0% | 14.2% | 13.6% | 1.00 |
| Lithium | 0% | 14.2% | 7.3% | 0.48 |
| Benzodiazepines | 0% | 23.8% | 23.6% | 1.00 |
| Single episode | 50% | 33.3% | 28.4% | 0.64 |
| Recurrent depression | 50% | 47.6% | 56.8% | 0.74 |
| Bipolar II | 0% | 14.2% | 11.9% | 0.79 |
| Dysthymia | 0% | 4.7% | 0% | 0.17 |
| Schizoaffective disorder | 0% | 0% | 1.8% | 1.00 |
| Adjustment disorder | 0% | 0% | 0.9% | 1.00 |
| Non-substrates of P-gp | | | | |
| N (% women) | 3 (100%) | 23 (52.1%) | 72 (52.7%) | 0.36 |
| Age | 45 ± 6.4 | 46.7 ± 2.9 | 50.4 ± 1.7 | 0.49 |

TABLE 6-continued

Genotype-dependent group characteristics for rs2032583
The group characteristics number of patients (% women), age, HDRS at inclusion, age at onset, illness duration in years, previous episodes, number of previous hospitalizations, duration of actual episode, ethnicity, co-medication and diagnosis are shown for each genotype. It was investigated in an ANOVA analysis whether there are significant differences between the CC, CT and TT groups (Sig). The Table shows the results of all patients, patients receiving substrates of P-gps and patients receiving non-P-gp-substrates.

|  | CC | CT | TT | Sig. |
|---|---|---|---|---|
| HAM-D at inclusion | 35.6 ± 5.3 | 27.1 ± 1.3 | 26.6 ± 0.7 | 0.07 |
| Age at onset | 31.3 ± 12.5 | 39.3 ± 2.9 | 37.4 ± 1.7 | 0.66 |
| Illness duration (years) | 13.6 ± 6.3 | 7.1 ± 1.5 | 12.9 ± 1.8 | 0.23 |
| Previous episodes | 1 ± 1 | 1.7 ± 0.2 | 2.3 ± 0.4 | 0.62 |
| Previous hospitalization | 0 ± 0 | 0.6 ± 0.2 | 2.7 ± 1.3 | 0.64 |
| Duration of actual | 46.3 ± 15 | 23 ± 4.1 | 42.8 ± 9.1 | 0.49 |
| Caucasian | 100% | 100% | 100% |  |
| German origin | 100% | 89.4% | 83% | 0.80 |
| Neuroleptics | 66.6% | 0% | 22.2% | 0.002 |
| Mood stabilizers | 0% | 4.3% | 11.1% | 0.59 |
| Lithium | 0% | 0% | 4.1% | 1.00 |
| Benzodiazepines | 33.3% | 30.4% | 30.5% | 1.00 |
| Single episode | 66.6% | 26% | 40.8% | 0.20 |
| Recurrent depression | 33.3% | 69.5% | 45% | 0.09 |
| Bipolar II | 0% | 4.3% | 14% | 0.50 |
| Dysthymia | 0% | 0% | 0% |  |
| Schizoaffective disorder | 0% | 0% | 0% |  |
| Adjustment disorder | 0% | 0% | 0% |  |

TABLE 7

Information on genotyped SNPs. Position according to Human Reference Sequence. SNP-Information was retrieved from dbSNP.

| SNP ID | Position | Gene | Function | Alleles | HWE-p-value | MAF | % genotyped |
|---|---|---|---|---|---|---|---|
| rs4148809 | 86747914 | ABCB4 | intron | A/G | 0.82 | 0.411 | 71.2 |
| rs2888611 | 86748321 | ABCB4 | intron | C/G | 0.70 | 0.172 | 71.4 |
| rs1922239 | 86751465 | ABCB4 | untranslated | C/G |  | not polymorph | 66.4 |
| rs6979325 | 86751910 | ABCB4 | locus | A/C | 0.46 | 0.044 | 71.4 |
| rs10280466 | 86751997 | ABCB4 | locus | G/T |  | not polymorph | 70.5 |
| rs2178658 | 86766673 |  | unknown | G/T | 0.76 | 0.233 | 71.4 |
| rs7789645 | 86767254 |  | unknown | C/G | 1.00 | 0.175 | 71.6 |
| rs7793196 | 86767498 |  | unknown | A/G | 1.00 | 0.175 | 71.4 |
| rs1055305 | 86777342 |  | locus | A/C |  | not polymorph | 61.9 |
| rs1055302 | 86777567 |  | locus | A/G | 0.34 | 0.133 | 76.4 |
| rs17064 | 86778121 | ABCB1 | untranslated | A/T | 0.57 | 0.055 | 61.3 |
| rs2235048 | 86783162 | ABCB1 | intron | C/T | 0.32 | 0.451 | 94.6 |
| rs1045642 | 86783296 | ABCB1 | coding-non- and synon | A/C/G/T | 0.63 | 0.446 | 97.5 |
| rs6949448 | 86786465 | ABCB1 | intron | C/T | 0.04 | 0.446 | 71.4 |
| rs7779562 | 86789467 | ABCB1 | intron | C/G | 1.00 | 0.030 | 89.6 |
| rs2235044 | 86790476 | ABCB1 | coding-synon | A/G |  | not polymorph | 57 |
| rs2235067 | 86794573 | ABCB1 | intron | A/G | 0.56 | 0.106 | 76.6 |
| rs4148744 | 86795425 | ABCB1 | intron | C/T | 1.00 | 0.038 | 64.9 |
| rs4148743 | 86795741 | ABCB1 | intron | A/G | 0.12 | 0.479 | 64.6 |
| rs4148740 | 86796754 | ABCB1 | intron | C/T | 0.28 | 0.116 | 71.2 |
| rs10280101 | 86798236 | ABCB1 | intron | A/C | 0.56 | 0.111 | 70.3 |
| rs7787082 | 86801702 | ABCB1 | intron | A/G | 0.05 | 0.152 | 70.3 |
| rs2032583 | 86805212 | ABCB1 | intron | C/T | 0.47 | 0.113 | 98 |
| rs2032582 | 86805269 | ABCB1 | coding-nonsynon | A/C/G/T | 0.37 | 0.444 | 74.5 |
| rs9282563 | 86805296 | ABCB1 | coding-synon | C/T | 1.00 | 0.002 | 69.6 |
| rs4148739 | 86805700 | ABCB1 | intron | A/G | 0.28 | 0.115 | 71.4 |
| rs11983225 | 86806171 | ABCB1 | intron | C/T | 0.40 | 0.117 | 70.3 |
| rs4148738 | 86807700 | ABCB1 | intron | A/G | 0.19 | 0.448 | 89.4 |
| rs10248420 | 86809637 | ABCB1 | intron | A/G | 0.07 | 0.150 | 70 |
| rs2235040 | 86810401 | ABCB1 | intron | A/G | 0.16 | 0.113 | 73.6 |
| rs12720067 | 86814007 | ABCB1 | intron | A/G | 0.25 | 0.111 | 71.2 |
| rs1922242 | 86818318 | ABCB1 | intron | A/T | 0.18 | 0.439 | 63.1 |
| rs2235046 | 86818717 | ABCB1 | intron | A/G | 0.08 | 0.444 | 95 |
| re2235036 | 86819922 | ABCB1 | coding-nonsynon | A/G |  | not polymorph | 71.8 |
| rs2235013 | 86823277 | ABCB1 | intron | A/G | 0.26 | 0.500 | 71.4 |
| rs2235012 | 86823378 | ABCB1 | coding-synon | C/G |  | not polymorph | 71.6 |
| rs2235035 | 86823737 | ABCB1 | intron | C/T | 0.53 | 0.345 | 70.3 |

TABLE 7-continued

Information on genotyped SNPs. Position according to Human Reference Sequence. SNP-Information was retrieved from dbSNP.

| SNP ID | Position | Gene | Function | Alleles | HWE-p-value | MAF | % genotyped |
|---|---|---|---|---|---|---|---|
| rs2235033 | 86823794 | ABCB1 | intron | C/T | 0.09 | 0.499 | 89.6 |
| rs2235032 | 86824033 | ABCB1 | intron | G/T | | not polymorph | 70.5 |
| rs2032588 | 86824094 | ABCB1 | intron | C/T | 1.00 | 0.054 | 62.8 |
| rs1128503 | 86824252 | ABCB1 | coding-synon | C/T | 0.57 | 0.435 | 71.4 |
| rs2229109 | 86824460 | ABCB1 | coding-nonsynon | A/G | 0.38 | 0.038 | 73.4 |
| rs2235030 | 86824577 | ABCB1 | intron | C/T | | not polymorph | 64.2 |
| rs2235029 | 86824586 | ABCB1 | intron | G/T | | not polymorph | 64.4 |
| rs10276036 | 86824849 | ABCB1 | intron | C/T | 0.57 | 0.435 | 71.2 |
| rs1922240 | 86828005 | ABCB1 | intron | C/T | 0.54 | 0.351 | 71.2 |
| rs2235023 | 86835103 | ABCB1 | intron | A/G | 1.00 | 0.066 | 74.8 |
| rs17407959 | 86840184 | ABCB1 | coding-synon | A/T | | not polymorph | 71.6 |
| rs17407952 | 86840185 | ABCB1 | coding-nonsynon | G/T | | not polymorph | 71.6 |
| rs1202169 | 86840501 | ABCB1 | intron | A/G | 0.20 | 0.429 | 95 |
| rs1202168 | 86840613 | ABCB1 | intron | C/T | 0.74 | 0.441 | 75 |
| rs1202167 | 86841710 | ABCB1 | intron | A/G | 0.55 | 0.431 | 64 |
| rs2235019 | 86843954 | ABCB1 | intron | G/T | 1.00 | 0.012 | 64.6 |
| rs2235018 | 86844016 | ABCB1 | intron | A/G | 1.00 | 0.002 | 64.9 |
| rs2235017 | 86844024 | ABCB1 | intron | C/T | 1.00 | 0.012 | 64.9 |
| rs2235016 | 86844063 | ABCB1 | intron | G/T | | not polymorph | 63.3 |
| rs2235015 | 86844215 | ABCB1 | intron | G/T | 0.60 | 0.168 | 92.6 |
| rs2235014 | 86844266 | ABCB1 | intron | C/T | | not polymorph | 64.9 |
| rs6950978 | 86845118 | ABCB1 | intron | A/T | 0.61 | 0.333 | 70.9 |
| rs10256836 | 86845424 | ABCB1 | intron | C/G | 0.80 | 0.331 | 71.4 |
| rs10264990 | 86847266 | ABCB1 | intron | C/T | 0.90 | 0.351 | 70.3 |
| rs1202179 | 86848930 | ABCB1 | intron | A/G | 0.90 | 0.334 | 77.3 |
| rs1989831 | 86850130 | ABCB1 | intron | A/T | 0.79 | 0.338 | 64.6 |
| rs1202172 | 86855625 | ABCB1 | intron | G/T | 0.75 | 0.334 | 98.2 |
| rs1202171 | 86855696 | ABCB1 | intron | A/T | 0.90 | 0.335 | 76.6 |
| rs17327442 | 86857641 | ABCB1 | intron | A/T | 0.37 | 0.149 | 71.2 |
| rs4148733 | 86857883 | ABCB1 | intron | C/T | 0.23 | 0.147 | 64.2 |
| rs1202186 | 86857909 | ABCB1 | intron | A/G | 1.00 | 0.329 | 64 |
| rs1202185 | 86858035 | ABCB1 | intron | A/G | 0.79 | 0.338 | 64.6 |
| rs1202182 | 86859955 | ABCB1 | intron | C/T | 0.60 | 0.340 | 64.6 |
| rs1202181 | 86860801 | ABCB1 | intron | C/T | 0.66 | 0.327 | 55.4 |
| rs2188525 | 86869423 | ABCB1 | intron | G/T | 1.00 | 0.035 | 71.6 |
| rs2235074 | 86869697 | ABCB1 | intron | C/T | 1.00 | 0.038 | 62.8 |
| rs2214102 | 86874152 | ABCB1 | untranslated | A/G | 0.15 | 0.103 | 55.9 |
| rs3213619 | 86874844 | ABCB1 | untranslated | C/T | | not polymorph | 62.8 |
| rs2188524 | 86875086 | ABCB1 | untranslated | A/G | | not polymorph | 64.6 |
| rs4728709 | 86878253 | ABCB1 | untranslated | A/G | 1.00 | 0.056 | 70.3 |
| rs4148731 | 86883980 | ABCB1 | untranslated | C/T | 1.00 | 0.021 | 64.4 |
| rs4148730 | 86884002 | ABCB1 | untranslated | C/T | 1.00 | 0.019 | 64.2 |
| rs13233308 | 86889611 | ABCB1 | untranslated | C/T | 0.43 | 0.489 | 71.2 |
| rs4604363 | 86898847 | ABCB1 | untranslated | A/G | | not polymorph | 64.6 |
| rs2157928 | 86903055 | ABCB1 | untranslated.intron | C/T | | not polymorph | 64.4 |
| rs4148729 | 86907037 | ABCB1 | untranslated.intron | A/C | 0.15 | 0.024 | 64.9 |
| rs10264856 | 86907232 | ABCB1 | untranslated.intron | A/G | 1.00 | 0.050 | 88.3 |
| rs2157926 | 86915151 | ABCB1 | untranslated.intron | A/T | 1.00 | 0.054 | 64.4 |
| rs4148728 | 86915468 | ABCB1 | untranslated.intron | A/C | | not polymorph | 64.4 |
| rs10246878 | 86920292 | ABCB1 | untranslated.intron | A/G | 0.54 | 0.239 | 71.2 |
| rs10267099 | 86923411 | ABCB1 | untranslated.intron | A/G | 0.21 | 0.237 | 89.6 |
| rs7796247 | 86969037 | ABCB1 | untranslated.intron | A/G | 0.13 | 0.019 | 89.6 |
| rs916715 | 86971580 | ABCB1 | untranslated.intron | C/T | | not polymorph | 64 |
| rs2188529 | 86977122 | ABCB1 | untranslated.intron | A/T | 1.00 | 0.018 | 62.4 |
| rs3747802 | 86987237 | | locus.intron | C/T | | not polymorph | 60.4 |

TABLE 7-continued

Information on genotyped SNPs. Position according to Human Reference Sequence. SNP-Information was retrieved from dbSNP.

| SNP ID | Position | Gene | Function | Alleles | HWE-p-value | MAF | % genotyped |
|---|---|---|---|---|---|---|---|
| rs4148727 | 86987417 | | locus.intron | C/T | 0.15 | 0.024 | 64.9 |
| rs10227683 | 86987607 | | locus.intron | C/T | | not polymorph | 71.2 |
| rs10275625 | 87009899 | | intron | C/T | 0.13 | 0.019 | 89.6 |

TABLE 8

Genotype-dependent group characteristics for rs2235015
The group characteristics number of patients (% women), age, HDRS at inclusion, age at onset, illness duration in years, previous episodes, number of previous hospitaiizations, duration of actual episode, ethnicity, co-medication and diagnosis are shown for each genotype. It was investigated in an ANOVA analysis whether there are significant differences between the CC, CT and TT groups (Sig). The Table shows the results of all patients, patients receiving substrates of P-gps and patients receiving non-P-gp-substrates.

| | GG | GT | TT | Sig. |
|---|---|---|---|---|
| All patients | | | | |
| N (% women) | 286 (58.7%) | 112 (52.6%) | 13 (61.5%) | 0.51 |
| Age | 49 ± 0.8 | 46.9 ± 1.3 | 48.6 ± 3.5 | 0.44 |
| HAM-D at inclusion | 26.6 ± 0.3 | 26.3 ± 0.6 | 27.7 ± 2.1 | 0.75 |
| Age at onset | 36.9 ± 0.9 | 35.7 ± 1.4 | 41.9 ± 5.2 | 0.38 |
| Illness duration (years) | 12.1 ± 0.7 | 11.3 ± 1 | 6.7 ± 2.4 | 0.30 |
| Previous episodes | 2.4 ± 0.3 | 3 ± 0.5 | 1.3 ± 0.4 | 0.36 |
| Previous hospitalization | 1.7 ± 0.3 | 1.3 ± 0.2 | 0.8 ± 0.2 | 0.68 |
| Duration of actual | 39.5 ± 4.2 | 40.1 ± 6.5 | 41.3 ± 11.7 | 0.99 |
| Caucasian | 100% | 100% | 100% | |
| German origin | 87.4% | 79.5% | 100% | 0.10 |
| Neuroleptics | 18.5% | 13.3% | 38.4% | 0.07 |
| Mood stabilizers | 18.8% | 16% | 7.6% | 0.60 |
| Lithium | 7.3% | 7.2% | 0% | 0.93 |
| Benzodiazepines | 30.7% | 30.3% | 30.7% | 1.00 |
| Single episode | 34.9% | 26.7% | 38.4% | 0.25 |
| Recurrent depression | 51.5% | 58.9% | 53.8% | 0.42 |
| Bipolar II | 11.3% | 13.3% | 7.6% | 0.86 |
| Dysthymia | 0.3% | 0.8% | 0% | 0.52 |
| Schizoaffective disorder | 0.7% | 0% | 0% | 1.00 |
| Adjustment disorder | 1% | 0% | 0% | 0.60 |
| Substrates of P-gp | | | | |
| N (% women) | 96 (62.5%) | 33 (51.5%) | 3 (33.3%) | 0.36 |
| Age | 45.8 ± 1.5 | 43.4 ± 2.4 | 48.3 ± 6.6 | 0.68 |
| HAM-D at inclusion | 26.7 ± 0.6 | 25.9 ± 1.4 | 28.3 ± 0.8 | 0.76 |
| Age at onset | 34.1 ± 1.5 | 33.4 ± 2.6 | 47.6 ± 6.8 | 0.30 |
| Illness duration (years) | 11.7 ± 1.1 | 10.3 ± 1.4 | 0.6 ± 0.3 | 0.19 |
| Previous episodes | 2.9 ± 0.6 | 1.4 ± 0.2 | 0.3 ± 0.3 | 0.29 |
| Previous hospitalization | 1.2 ± 0.1 | 0.7 ± 0.2 | 0.3 ± 0.3 | 0.13 |
| Duration of actual | 38.9 ± 7.1 | 33 ± 7.4 | 29.3 ± 9.6 | 0.88 |
| Caucasian | 100% | 100% | 100% | |
| German origin | 84.5% | 88% | 100% | 1.00 |
| Neuroleptics | 14.5% | 24.2% | 0% | 0.38 |
| Mood stabilizers | 16.6% | 6% | 0% | 0.26 |
| Lithium | 9.4% | 6% | 0% | 0.79 |
| Benzodiazepines | 21.8% | 24.2% | 33.3% | 0.75 |
| Single episode | 30.5% | 24.2% | 66.6% | 0.29 |
| Recurrent depression | 52% | 66.6% | 33.3% | 0.29 |
| Bipolar II | 13.6% | 6% | 0% | 0.55 |
| Dysthymia | 0% | 3% | 0% | 0.27 |
| Schizoaffective disorder | 2.1% | 0% | 0% | 1.00 |
| Adjustment disorder | 1% | 0% | 0% | 1.00 |
| Non-substrates of P-gp | | | | |
| N (% women) | 62 (51.6%) | 30 (53.3%) | 4 (100%) | 0.22 |
| Age | 49.7 ± 1.8 | 49.9 ± 2.6 | 41.7 ± 8.1 | 0.55 |
| HAM-D at inclusion | 27.1 ± 0.8 | 26.4 ± 1.1 | 30.7 ± 5.7 | 0.48 |
| Age at onset | 37.7 ± 1.9 | 38.5 ± 2.6 | 33.2 ± 10.2 | 0.80 |
| Illness duration (years) | 11.9 ± 1.9 | 11.3 ± 2.2 | 8.5 ± 4 | 0.89 |
| Previous episodes | 1.6 ± 0.3 | 3.2 ± 0.9 | 1.5 ± 0.9 | 0.13 |
| Previous hospitalization | 2.6 ± 1.5 | 1.5 ± 0.4 | 0 ± 0 | 0.80 |
| Duration of actual | 40 ± 9 | 36.8 ± 12.9 | 30.7 ± 15.3 | 0.95 |
| Caucasian | 100% | 100% | 100% | |
| German origin | 88.2% | 76% | 100% | 0.42 |
| Neuroleptics | 20.9% | 10% | 50% | 0.11 |
| Mood stabilizers | 11.2% | 6.6% | 0% | 0.81 |
| Lithium | 4.8% | 0% | 0% | 0.60 |
| Benzodiazepines | 25.8% | 43.3% | 25% | 0.23 |
| Single episode | 44.2% | 26.6% | 50% | 0.22 |
| Recurrent depression | 42.6% | 66.6% | 25% | 0.049 |
| Bipolar II | 13.1% | 6.6% | 25% | 0.33 |
| Dysthymia | 0% | 0% | 0% | |
| Schizoaffective disorder | 0% | 0% | 0% | |
| Adjustment disorder | 0% | 0% | 0% | |

TABLE 9

Details with respect to animals, experimental and extraction procedures, and high-performance liquid chromatography.

| | Citalopram | Mirtazapine | Venlafaxine |
|---|---|---|---|
| Animals | | | |
| Gender | male | male | male |
| Group size [n] | 8 | 9 | 8 |
| Age [weeks] | 16-24 | 15-17 | 12-15 |
| Weight abcb1ab(−/−) | 31.2 ± 0.6 | 28.6 ± 0.3 | 30.6 ± 0.5 |
| Weight abcb1ab(+/+) | 29.8 ± 1.0 | 28.3 ± 0.6 | 29.9 ± 1.0 |

TABLE 9-continued

Details with respect to animals, experimental and extraction procedures, and high-performance liquid chromatography.

|  | Citalopram | Mirtazapine | Venlafaxine |
|---|---|---|---|
| Experimental procedure s.c. administration via osmotic pumps | 60 µg/day | 60 µg/day | 300 µg/day |
| Extraction procedures |  |  |  |
| Isoamyl alcohol (plasma extraction) | 0% | 0% | 0.5% |
| Isoamy alcohol (organ extraction) | 0% | 0% | 0.5% |
| High-performance liquid chromatography |  |  |  |
| Mobile phase gradient [% B] | 5-25 | 0-25 | 0-30 |
| Detection UV [nm] | 214 | 214 | 214 |
| Detection fluorescence ex/em [nm] | 230/300 | 295/370 | 225/305 |

B, acetonitrile;
ex, extinction;
em, emission

REFERENCES

Ambudkar, S. V., Dey, S., Hrycyna, C. A., Ramachandra, M., Pastan, I., and Gottesman, M. M., (1999). Biochemical, cellular, and pharmacological aspects of the multidrug transporter. Annu. Rev. Pharmacol. Toxicol. 39, 361-398.

Binder, E. B., Salyakina, D., Lichtner, P., Wochnik, G. M., Ising, M., Pütz, B., Papiol, S., Seaman, S., Lucae, S., Kohli, M. A., Nickel. T., Künzel, H. E., Fuchs, B., Majer, M., Pfennig, A., Kern, N., Brunner, J., Modell, S., Baghai, T., Deiml, T., Zill, P., Bondy, B., Rupprecht, R., Messer, T., Köhnlein, O., Dabitz, H., Brückl, T., Müller, N., Pfister, H., Lieb, R., Mueller, J. C., Löhmussaar, E., Strom, T. M., Bettecken, T., Meitinger, T., Uhr, M., Rein, T., Holsboer, F., and Müller-Myhsok, B. (2004). Polymorphisms in FKBP5 are associated with increased recurrence of depressive episodes and rapid response to antidepressant treatment. Nat. Genet. 36, 1319-1325.

Brinkmann, U. (2002). Functional polymorphisms of the human multidrug resistance (MDR1) gene: correlation with P glycoprotein expression and activity in vivo. Novartis Found Symp. 243, 207-210; discussion 210-217; 231-235.

Callen, D. F., Baker, E., Simmers, R. N., Seshadri, R., and Roninson, I. B. (1987). Localization of the human multiple drug resistance gene, MDR1, to 7q21.1. Hum. Genet. 77, 142-144.

Cascorbi, I., Gerloff, T., Johne, A., Meisel, C., Hoffmeyer, S., Schwab, M., Schaeffeler, E., Eichelbaum, M., Brinkmann, U., and Roots, I. (2001). Frequency of single nucleotide polymorphisms in the P-glycoprotein drug transporter MDR1 gene in white subjects. Clin. Pharmacol. Ther. 69, 169-174.

Chin, J. E., Soffir, R., Noonan, K. E., Choi, K., and Roninson, I. B. (1989). Structure and expression of the human MDR (P-glycoprotein) gene family. Mol. Cell. Biol. 9, 3808-3820.

Cordon-Cardo, C., O'Brien, J. P., Casals, D., Rittman-Grauer, L., Biedler, J. L., Melamed, M. R., and Bertino, J. R. (1989). Multidrug resistance gene (P-glycoprotein) is expressed by endothelial cells at blood-brain barrier sites. Proc. Natl. Acad. Sci. USA 86, 695-698.

Devault, A., and Gros, P. (1990). Two members of the mouse mdr gene family confer multidrug resistance With overlapping but distinct drug specificities. Mol. Cell. Biol. 10, 1652-1663.

Eichelbaum, M., Fromm, M. F., and Schwab, M. (2004). Clinical aspects of the MDR1 (ABCB1) gene polymorphism. Ther. Drug. Monit. 26, 180-185.

Fisher, R. A. (1932). Statistical Methods for Research Workers. Oliver and Boyd, London Gabriel, S. B., Schaffner, S. F., Nguyen, H., Moore, J. M., Roy, J., Blumenstiel, B., Higgins, J., DeFelice, M., Lochner, A., Faggart, M., Neen Liu-Cordero, S., Rotimi, C., Adeyemo, A., Cooper, R., Ward, R., Lander, E. S., Daly, M. J., and Altshuler, D. (2002). The structure of haplotype blocks in the human genome. Science 296, 2225-2229.

Grauer, M. T., and Uhr, M. (2004). P-glycoprotein reduces the ability of amitriptyline to cross the blood brain barrier in mice after a 10-day administration of amitriptyline. J. Psychopharmacol. 18, 66-74.

Hill, W. G., and Robertson, A. (1968). Linkage disequilibrium in finite populations. Theoret. Appl. Genet. 38, 226-231.

Hoffmeyer, S., Burk, O., von Richter, O., Arnold, H. P., Brockmoller, J., Johne, A., Cascorbi, I., Gerloff, T., Roots, I., Eichelbaum, M., and Brinkmann, U. (2000). Functional polymorphisms of the human multidrug resistance gene: multiple sequence variations and correlation of one allele with P-glycoprotein expression and activity in vivo. Proc. Natl. Acad. Sci. USA 97, 3473-3478.

Ito, S., Ieiri, I., Tanabe, M., Suzuki, A., Higuchi, S., and Otsubo, K. (2001). Polymorphism of the ABC transporter genes, MDR1, MRP1 and MRP2/cMOAT, in healthy Japanese subjects. Pharmacogenetics 11, 175-184.

Kim, R. B., Leake, B. F., Chao, E. F., Dresser, G. K., Kubba, S. V., Schwarz, U. I., Taylor, A., Xie, H. G., McKinsey, J., Zhou, S., Lan, L. B., Schuetz, J. D., Schuetz, E. G., and Wilkinson, G. R. (2001). Identification of functionally variant MDR1 alleles among European Americans and African Americans. Clin. Pharmacol. Ther. 70, 189-199.

Kim, R. B. (2002). MDR1 single nucleotide polymorphisms: multiplicity of haplotypes and functional consequences. Pharmacogenetics 12, 425-427

Kimchi-Sarfaty, C., Oh, M. J., Kim, I.-W., Sauna, Z. E., Calcagno, A. M., Ambudkar, S. V., and Gottesman, M. M. (2007). A "silent" polymorphism in the MDR1 gene changes substrate specificity. Science 315, 525-528.

Kioka, N., Tsubota, J., Kakehi, Y., Komano, T., Gottesman, M. M., Pastan, I., and Ueda, K. (1989). P-glycoprotein gene (MDR1) cDNA from human adrenal: normal P-glycoprotein carries Gly185 with an altered pattern of multidrug resistance. Biochem. Biophys. Res. Commun. 162, 224-231.

Kroetz, D. L., Pauli-Magnus, C., Hodges, L. M., Huang, C. C., Kawamoto, M., Johns, S. J., Stryke, D., Ferrin, T. E., DeYoung, J., Taylor, T., Carlson, E. J., Herskowitz, I., Giacomini, K. M., and Clark, A. G. (2003). Sequence diversity and haplotype structure in the human ABCB1 (MDR1, multidrug resistance transporter) gene. Pharmacogenetics 13, 481-494.

Künzel, H. E., Binder, E. B., Nickel, T., (sing, M., Fuchs, B., Majer, M., Pfennig, A., Ernst, G., Kern, N., Schmid, D. A., Uhr, M., Holsboer, F., and Modell, S. (2003). Pharmacological and nonpharmacological factors influencing hypothalamic-pituitary-adrenocortical axis reactivity in acutely depressed psychiatric in-patients, measured by the Dex-CRH test. Neuropsychopharmacology 28, 2169-2178.

McMahon, F. J., Buervenich, S., Charney, D., Lipsky, R., Rush A. J., Wilson A. F., Sorant A. J. M., Papanicolaou G. J., Laje G., Fava M., Trivedi M. H., Wisniewski S. R. and Manji, H. (2006). Variation in the Gene Encoding the Serotonin 2A Receptor Is Associated with Outcome of Antidepressant Treatment. Am. J. Hum. Genet. 78, 804-814.

Meijer, O. C., de Lange, E. C., Breimer, D. D., de Boer, A. G., Workel, J. O., and de Kloet, E. R. (1998). Penetration of dexamethasone into brain glucocorticoid targets is enhanced in mdr1A P-glycoprotein knockout mice. Endocrinology 139, 1789-1793.

Mickley, L. A., Lee, J. S., Weng, Z., Zhan, Z., Alvarez, M., Wilson, W., Bates, S. E., and Fojo, T. (1998). Genetic polymorphism in MDR-1: a tool for examining allelic expression in normal cells, unselected and drug-selected cell lines, and human tumors. Blood 91, 1749-1756.

Murray, C. J., and Lopez, A. D. (1996). Evidence-based health policy—lessons from the Global Burden of Disease Study. Science 274, 740-743.

Sakaeda, T., Nakamura, T., and Okumura, K. (2003). Pharmacogenetics of MDR1 and its impact on the pharmacokinetics and pharmacodynamics of drugs. Pharmacogenomics, 4, 397-410.

Schinkel, A. H., Mayer, U., Wagenaar, E., Mol, C. A., van Deemter, L., Smit, J. J., van der Valk, M. A., Voordouw, A. C., Spits, H., van Tellingen, O., Zijlmans, J. M., Fibbe, W. E., and Borst, P. (1997). Normal viability and altered pharmacokinetics in mice lacking mdr1-type (drug-transporting) P-glycoproteins. Proc. Natl. Acad. Sci. USA 94, 4028-4033.

Schinkel, A. H., Wagenaar, E., Mol, C. A., and van Deemter, L. (1996). P-glycoprotein in the blood-brain barrier of mice influences the brain penetration and pharmacological activity of many drugs. J. Clin. Invest. 97, 2517-2524.

Stein, U., Walther, W., and Wunderlich, V. (1994). Point mutations in the mdr1 promoter of human osteosarcomas are associated with in vitro responsiveness to multidrug resistance relevant drugs. Eur. J. Cancer 30A, 1541-1545.

Tanabe, M., Ieiri, I., Nagata, N., Inoue, K., Ito, S., Kanamori, Y., Takahashi, M., Kurata, Y., Kigawa, J., Higuchi, S., Terakawa, N., and Otsubo, K. (2001). Expression of P-glycoprotein in human placenta: relation to genetic polymorphism of the multidrug resistance (MDR)-1 gene. J. Pharmacol. Exp. Ther. 297, 1137-1143.

Tang, K., Ngoi, S. M., Gwee, P. C., Chua, J. M., Lee, E. J., Chong, S. S., and Lee, C. G. (2002). Distinct haplotype profiles and strong linkage disequilibrium at the MDR1 multidrug transporter gene locus in three ethnic Asian populations. Pharmacogenetics 12, 437-450.

Tang, K., Wong, L. P., Lee, E. J., Chong, S. S., and Lee, C. G. (2004). Genomic evidence for recent positive selection at the human MDR1 gene locus. Hum. Mol. Genet. 13, 783-797.

Thiebaut, F., Tsuruo, T., Hamada, H., Gottesman, M. M., Pastan, I., and Willingham, M. C. (1987). Cellular localization of the multidrug resistance gene product P-glycoprotein in normal human tissues. Proc. Natl. Acad. Sci. USA 84, 7735-7738.

Trivedi, M. H., Rush, A. J., Wisniewski, S. R., Nierenberg, A. A., Warden, D., L., Norquist, G., Howland, R. H., Lebowitz, B., McGrath, P. J., Shores-Wilson, K., Biggs, M. M., Balasubramani, G. K., and Fava, M. (2006). Evaluation of outcomes with Citalopram for depression using measurement-based care in STAR*D: implications for clinical practice. Am. J. Psychiatry 163, 28-40.

Uhr, M., Steckler, T., Yassouridis, A., and Holsboer, F. (2000). Penetration of amitriptyline, but not of fluoketine, into brain is enhanced in mice with blood-brain barrier deficiency due to mdr1a P-glycoprotein gene disruption. Neuropsychopharmacology 22, 380-387.

Uhr, M., Holsboer, F., and Müller, M. B. (2002). Penetration of endogenous steroid hormones corticosterone, cortisol, aldosterone and progesterone into the brain is enhanced in mice deficient for both mdr1a and mdr1b P-glycoproteins. J. Neuroendocrinol. 14, 753-759.

Uhr, M., Grauer, M. T., and Holsboer, F. (2003). Differential enhancement of antidepressant penetration into the brain in mice with abcb1ab (mdr1 ab) P-glycoprotein gene disruption. Biol. Psychiatry 54, 840-846.

Uhr, M., and Grauer, M. T. (2003). abcb1ab P-glycoprotein is involved in the uptake of citalopram and trimipramine into the brain of mice. J. Psychiatr. Res. 37, 179-185.

Uhr, M., Namendorf, C., Grauer, M. T., Rosenhagen, M., and Ebinger, M. (2004). P-glycoprotein is a factor in the uptake of dextromethorphan, but not of melperone, into the mouse brain: evidence for an overlap in substrate spe between P-gp and CYP2D6. J. Psychopharmacol. 18, 509-515.

Uhr, M., Ebinger, M., Rosenhagen, M. C., and Grauer, M. T. (2005). The anti-Parkinson drug budipine is exported actively out of the brain by P-glycoprotein in mice. Neurosci. Lett. 383, 73-76.

Uhr, M., Grauer, M. T., Yassouridis, A., and Ebinger, M. (2007). Blood-brain barrier penetration and pharmacokinetics of amitriptyline and its metabolites in P-glycoprotein (abcb1ab) knock-out mice and controls. J. Psychiatric Res. 41, 179-188.

van de Vrie, W., Marquet, R. L., Stoter, G., de Bruijn, E. A., and Eggermont, A. M. (1998). In vivo model systems in P-glycoprotein-mediated multidrug resistance. Crit. Rev. Olin. Lab. Sci. 35, 1-57.

Westfall, P. H., and Young, S. S. (1993). Resampling-based multiple testing. John Wiley & Sons, New York.

Wigginton, J. E., Cutler, D. J., and Abecasis, G. R. (2005). A note on exact tests of Hardy-Weinberg equilibrium. Am. J. Hum. Genet. 76, 887-893.

The invention claimed is:
1. A method for detecting the minor C allele of the rs4148740 polymorphism in a patient, comprising:
   a) obtaining a blood sample from a patient suffering from depressive disorder, dysthymia, or bipolar disorder;
   b) extracting DNA from the blood sample to provide a DNA sample;
   c) contacting the DNA sample with at least one probe or primer capable of hybridizing with ABCB1 gene polymorphism rs4148740, and
   d) carrying out genotyping analysis to detect the minor C allele of the rs4148740 polymorphism.

2. The method according to claim 1, further comprising contacting the DNA sample with at least one additional probe or primer capable of determining the presence of a ABCB1 gene polymorphism in linkage disequilibrium with polymorphism rs4148740, wherein said ABCB1 gene polymorphism in linkage disequilibrium with polymorphism rs4148740 is selected from the group consisting of rs2235067, rs2032583, rs4148739, rs11983225, rs2235040, rs12720067, rs7787082, rs10248420, and combinations thereof.

3. The method of claim 1, wherein the genotyping analysis comprises the use of polymorphism-specific primers and/or probes.

4. The method of claim 1, wherein the genotyping analysis comprises a primer extension reaction.

5. The method of claim 1, wherein the genotyping analysis comprises a microarray analysis.

6. The method of claim 1, wherein the genotyping analysis comprises a mass-spectrometric analysis.

7. The method of claim 1, further comprising detecting a change in the function of the ABCB1 gene.

8. The method of claim 7, wherein detecting a change in the function of the ABCB1 gene comprises detecting the transport of specific substances at the blood-brain barrier.

* * * * *